(12) United States Patent
Burhans et al.

(10) Patent No.: US 9,034,857 B2
(45) Date of Patent: May 19, 2015

(54) METHODS FOR REDUCING SUPEROXIDE ANIONS IN EUKARYOTIC ORGANISMS

(75) Inventors: William C. Burhans, Buffalo, NY (US); Catherine E. Prudom Gineste, Harrisonburg, VA (US); Christopher P. Allen, Fort Collins, CO (US); Oleg Ursu, Albuquerque, NM (US); Anna Waller, Albuquerque, NM (US); Larry A. Sklar, Albuquerque, NM (US)

(73) Assignees: Health Research, Inc., Buffalo, NY (US); STC.UNM, Albuquerque, NM (US)

( * ) Notice: Subject to any disclaimer, the term of this patent is extended or adjusted under 35 U.S.C. 154(b) by 0 days.

(21) Appl. No.: 13/636,785

(22) PCT Filed: Mar. 24, 2011

(86) PCT No.: PCT/US2011/029740
§ 371 (c)(1),
(2), (4) Date: Dec. 28, 2012

(87) PCT Pub. No.: WO2011/119798
PCT Pub. Date: Sep. 29, 2011

(65) Prior Publication Data
US 2013/0150336 A1    Jun. 13, 2013

Related U.S. Application Data

(60) Provisional application No. 61/317,056, filed on Mar. 24, 2010, provisional application No. 61/346,275, filed on May 19, 2010, provisional application No. 61/347,992, filed on May 25, 2010, provisional application No. 61/361,111, filed on Jul. 2, 2010.

(51) Int. Cl.
 *A61K 31/498*    (2006.01)
 *A61K 31/58*    (2006.01)
 *A61K 31/56*    (2006.01)
 *C12Q 1/02*    (2006.01)

(52) U.S. Cl.
 CPC ............... *A61K 31/58* (2013.01); *A61K 31/498* (2013.01); *A61K 31/56* (2013.01); *G01N 2500/10* (2013.01); *G01N 2800/7009* (2013.01); *C12Q 1/025* (2013.01)

(58) Field of Classification Search
 IPC ................................................... A61K 31/498
 See application file for complete search history.

(56) References Cited

U.S. PATENT DOCUMENTS

| 5,714,481 A | 2/1998 | Schwartz et al. |
| 6,150,348 A | 11/2000 | Araneo et al. |

OTHER PUBLICATIONS

Aminian, B., et al., Correlation between Dehydroepiandrosterone Sulfate (DHEA-S) and Coronary Artery Disease, Iranian Journal of Endocrinology and Metabolism 2000, vol. 2, No. 2, pp. 107-111.
Bauer, M. et al., Starvation response in mouse liver shows strong correlation with life-span-prolonging processes, Physiol. Genomics 2004, vol. 17, pp. 230-244.

*Primary Examiner* — Svetlana M Ivanova
(74) *Attorney, Agent, or Firm* — Hodgson Russ LLP

(57) ABSTRACT

Provided are methods and compositions for reducing superoxide anions such that a prophylactic or therapeutic effect against conditions associated with excess oxidative stress achieved. The compositions and methods provide for reducing inflammation and for enhancing lifespan of eukaryotic organisms. A screen for identifying compounds that can be used in these methods is also provided.

1 Claim, 22 Drawing Sheets

Figure 1, continued
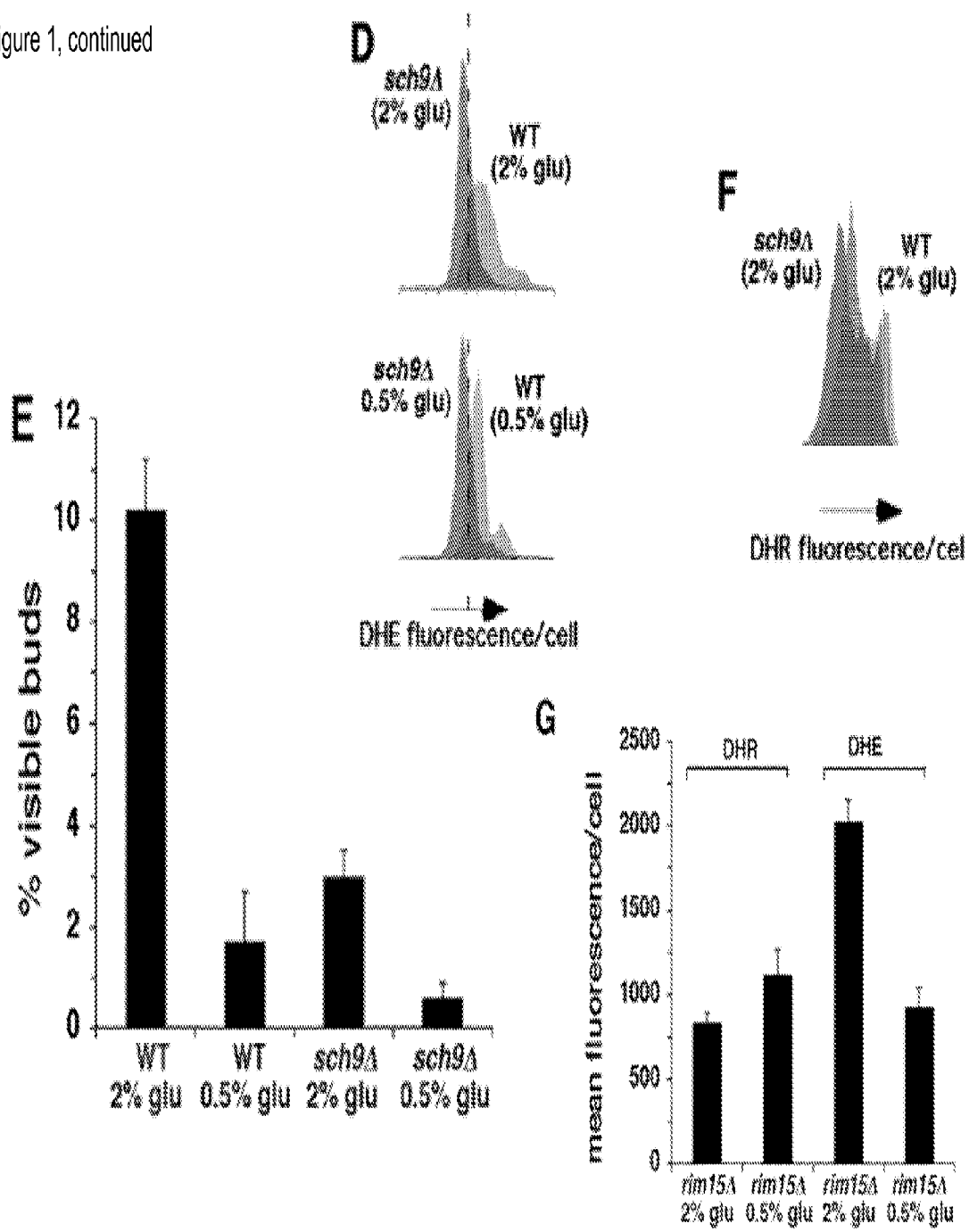

Figure 4
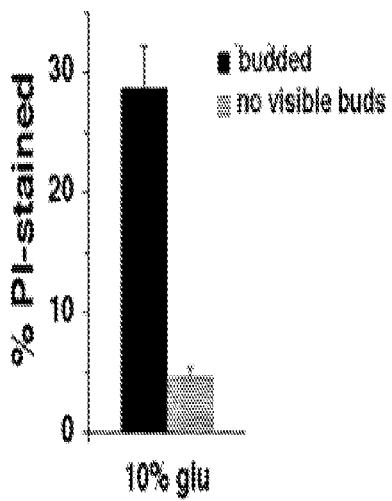
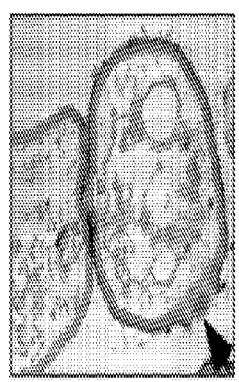
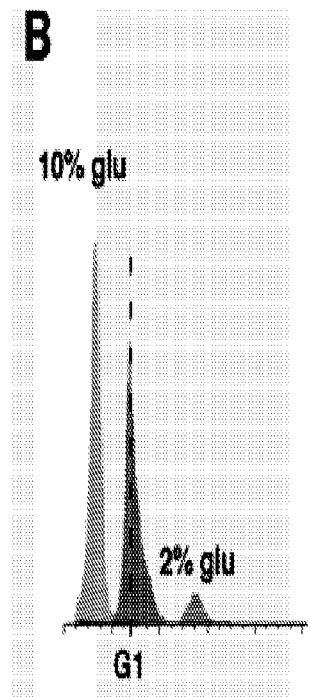
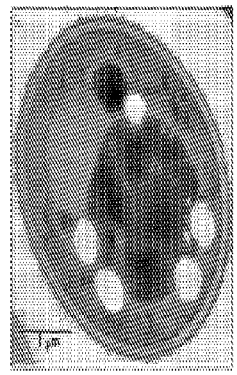
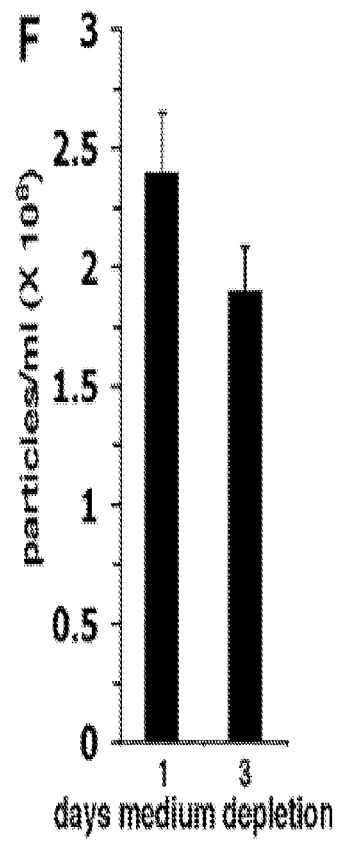

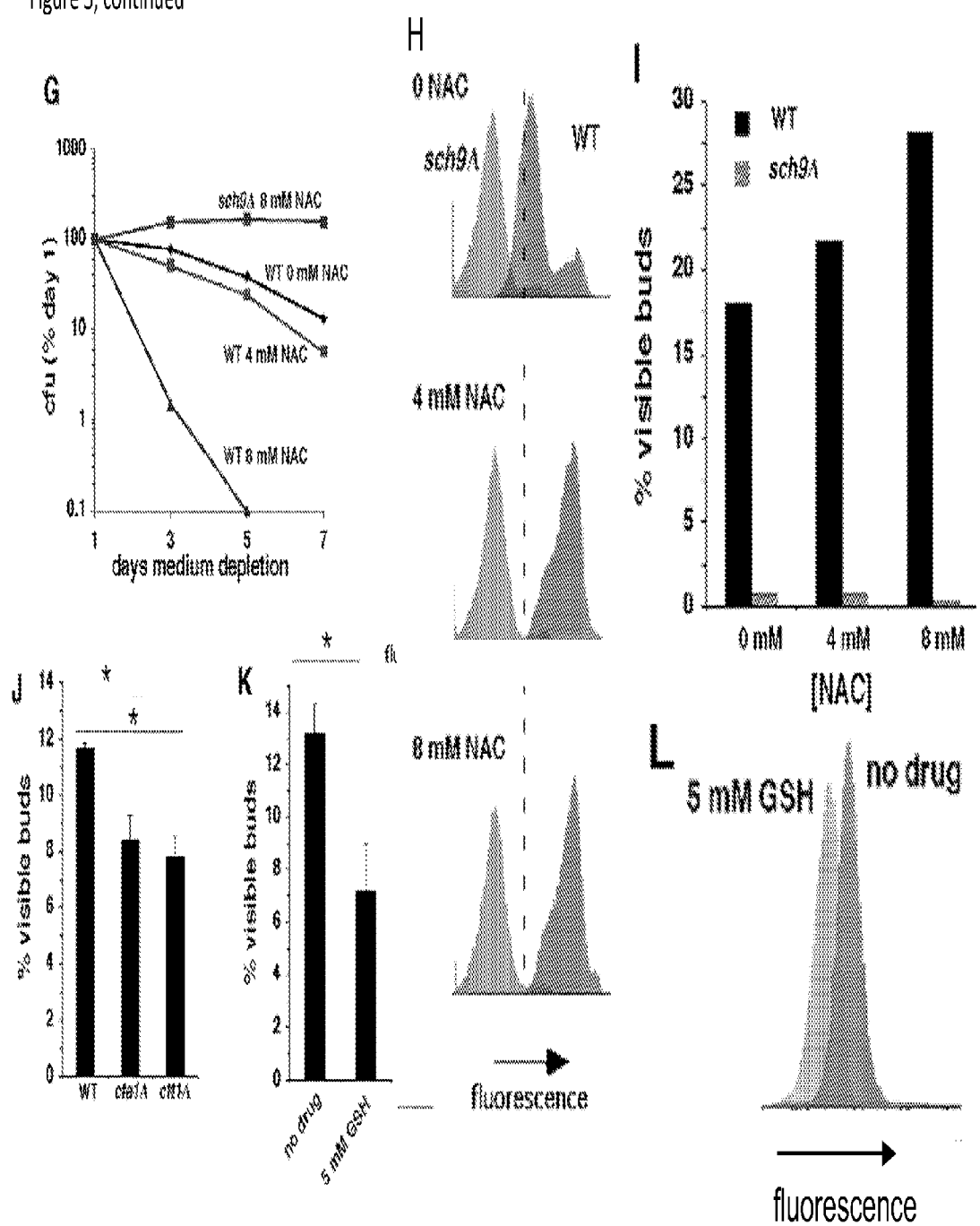
Figure 5, continued

Figure 10

| Strain | Genotype |
|---|---|
| DBY746 | MATa leu2-3,112 his3Δ1 trp1-2889 ura3-52 |
| DBY746 rim15Δ | MATa leu2-3,112 his3Δ1 trp1-2889 ura3-52 rim15Δ::TRP1 |
| DBY746 sch9Δ (PF102) | MATa leu2-3,112 his3Δ1 trp1-2889 ura3-52 sch9::URA3 |
| DBY746 sch9Δ rim15Δ | MATa leu2-3,112 his3Δ1 trp1-2889 ura3-52 sch9::URA3 rim15::LEU2 |
| BY4741 | MATa his3Δ leu2Δ met15Δ ura3Δ |
| BY4741 sic1Δ | MATa his3Δ leuΔ met15Δ ura3Δ YRL079W |
| BY4741 snf1Δ | MATa his3Delta1 leu2Δ met15Δ ura3Δ ΔYDR477W |
| BY 4742 | MATalpha his3Δ1 leu2Δ lys2Δ0 ura3Δ |
| BY 4742 cta1Δ | MATalpha his3Δ leu2Δ lys2Δ ura3Δ cta1Δ |
| BY 4742 ctt1Δ | MATalpha his3Δ leu2Δ lys2Δ ura3Δ ctt1Δ |
| W303-1A | MATa ade2-1 ura3-1 his3-11 trp1-1 leu2-3 can1-100 |
| MTy767 (W303 sic1Δ) | MATa ade2-1 ura3-1 his3-11 trp1-1 leu2-3 can1-100 sic1::URA3 |
| Y604 (W303 mec1-21) | MATa ade2-1 ura3-1 his3-11 trp1-1 leu2-3 can1-100 mec1-21 |
| W303 rad53-21 | MATa ade2-1 ura3-1 his3-11 trp1-1 leu2-3 can1-100 rad53-21 |

Figure 11
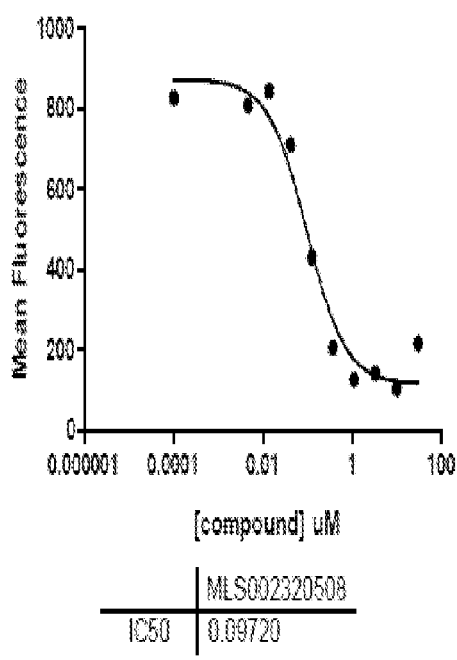
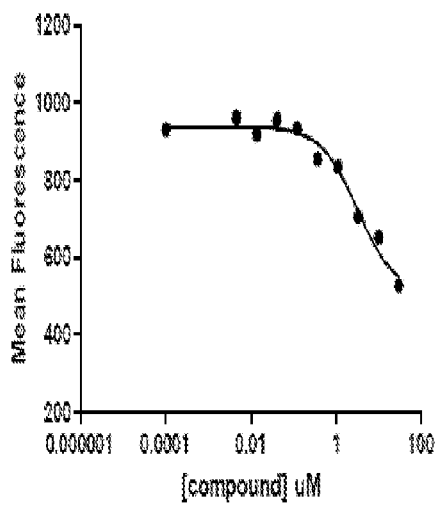
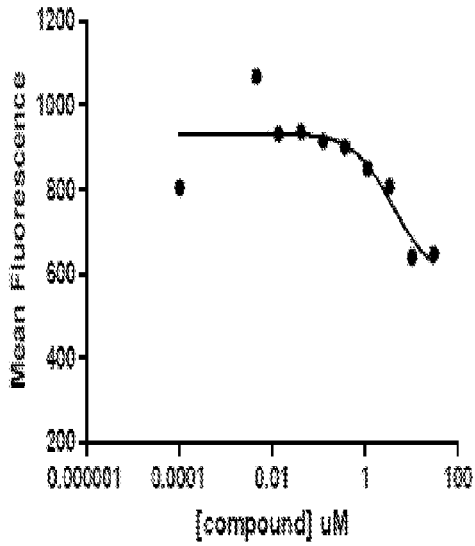
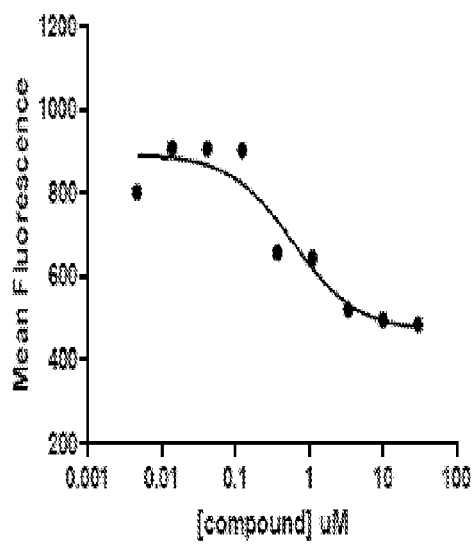

Figure 12
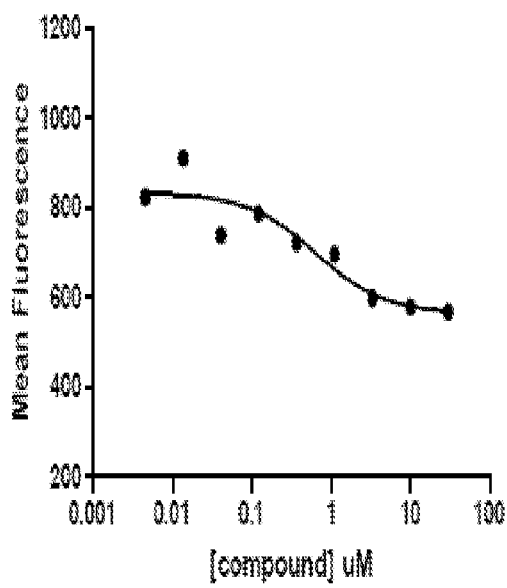
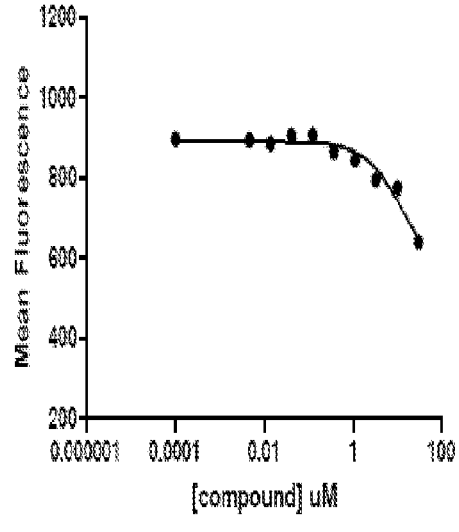
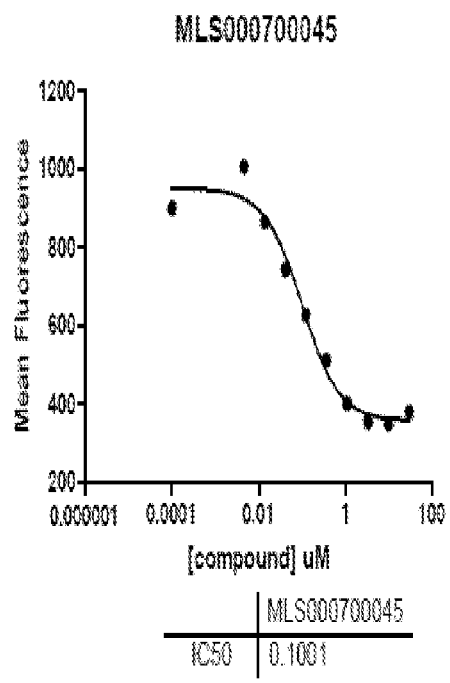
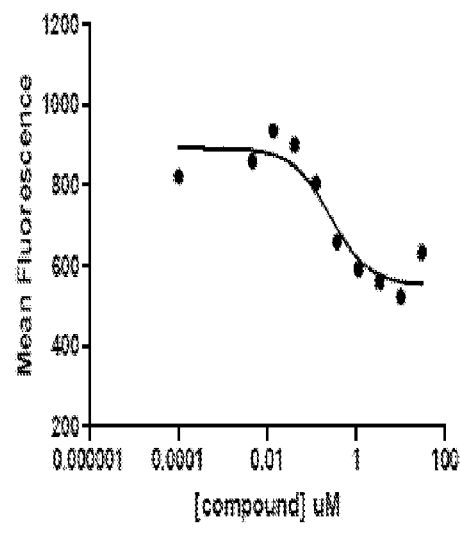

Figure 13
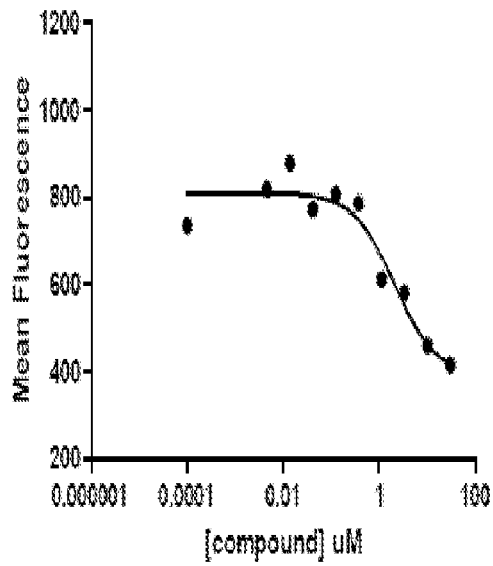
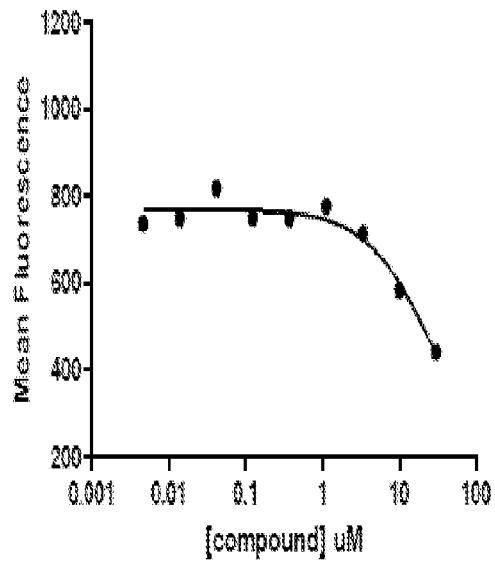
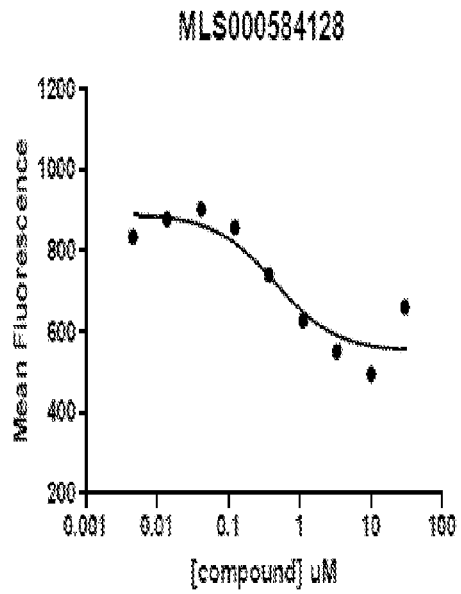
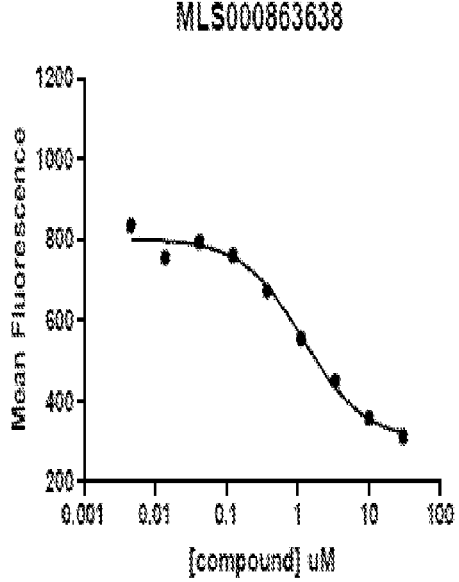

Figure 14
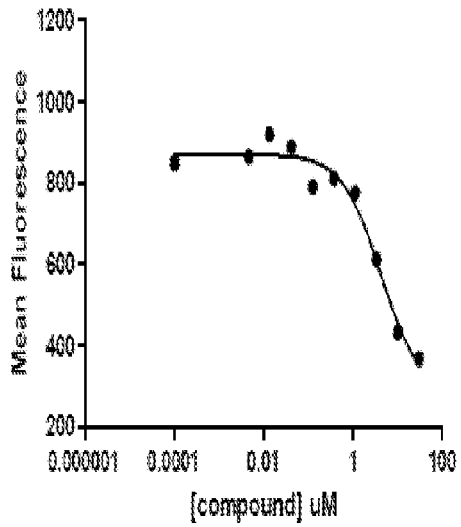
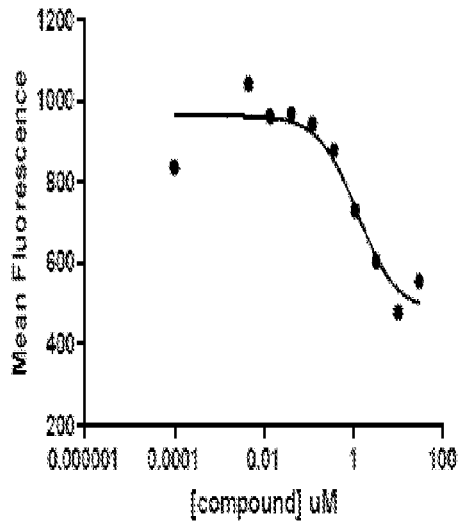
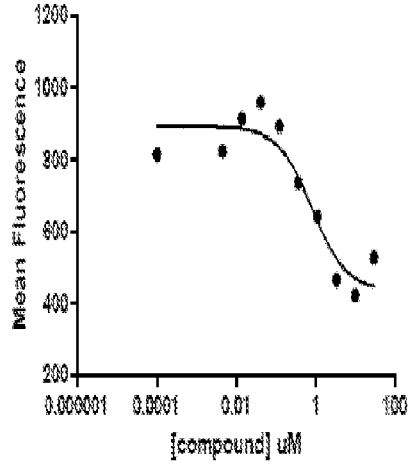
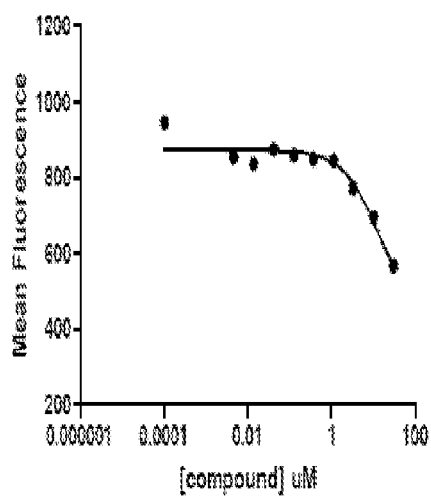

Figure 15
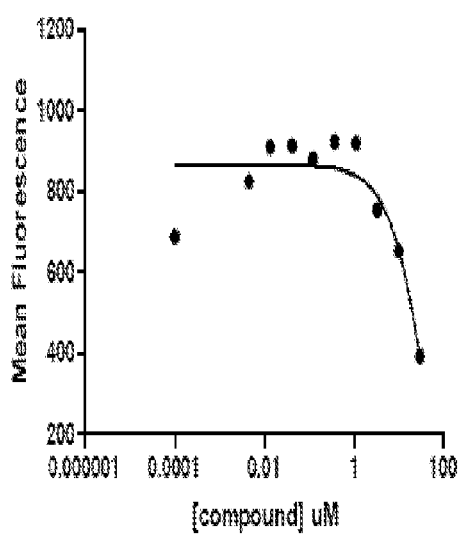
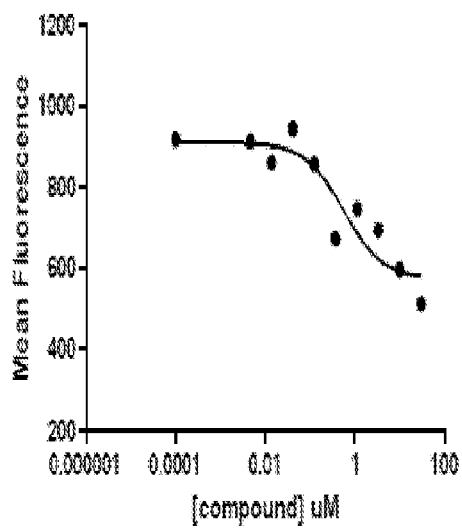
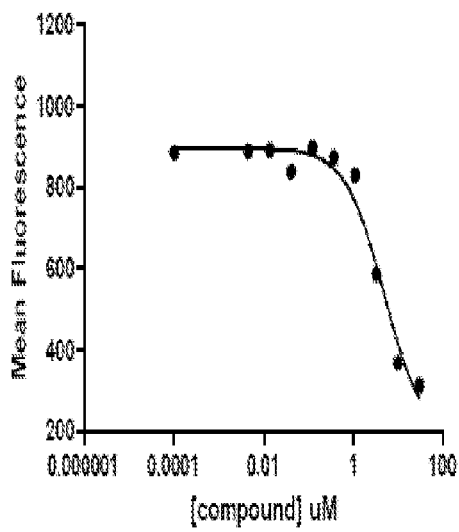
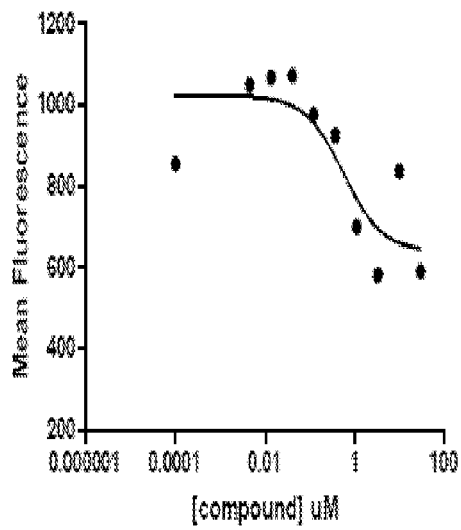

Figure 17
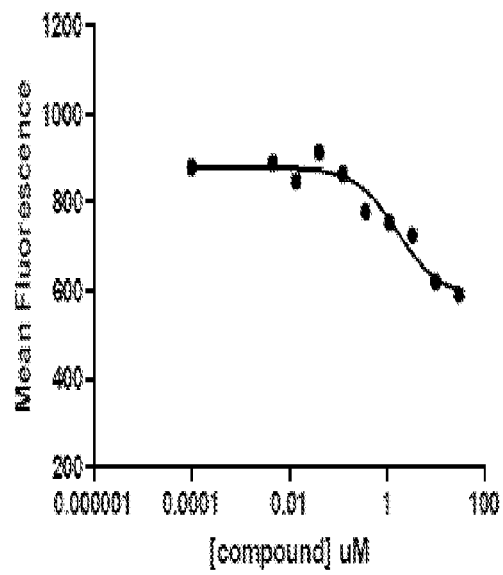
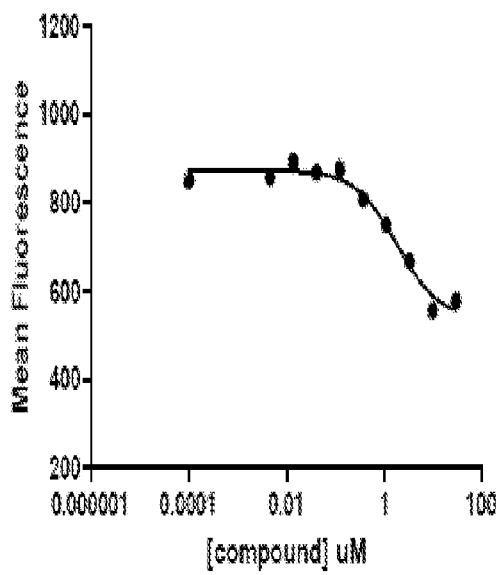
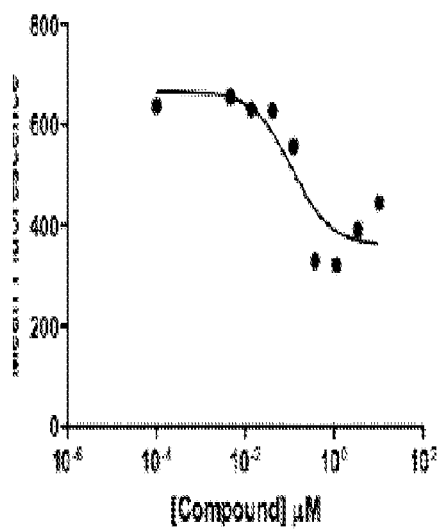
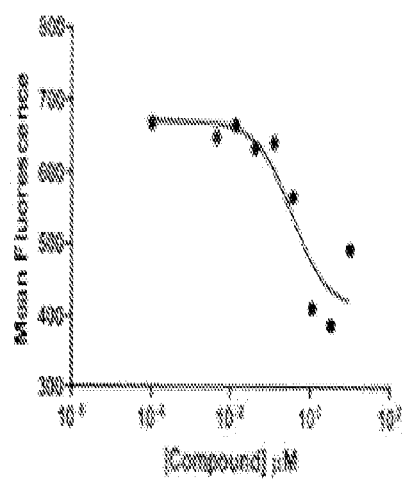

Figure 18
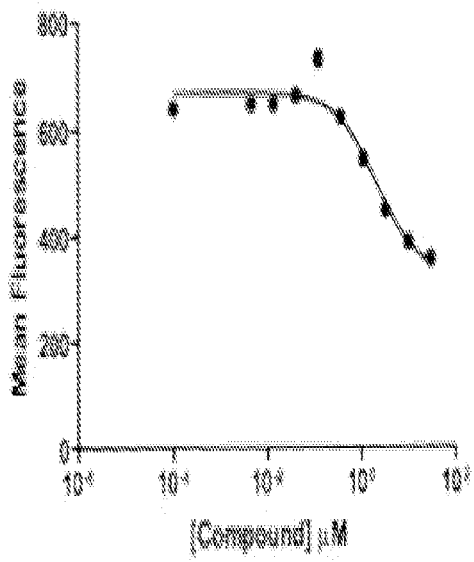
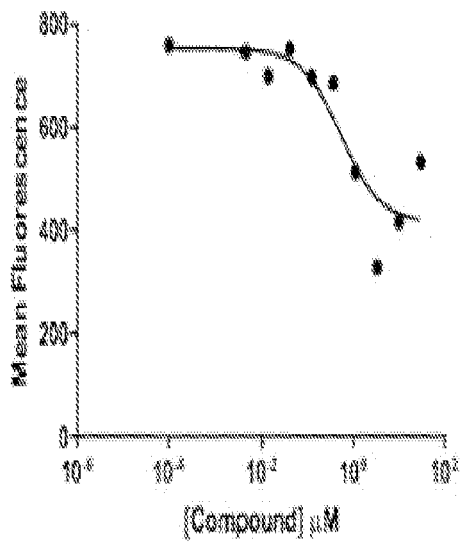
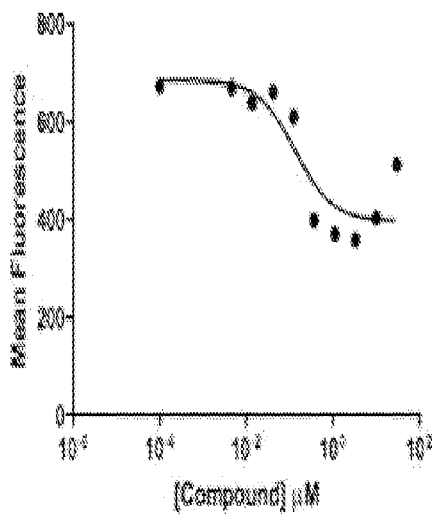
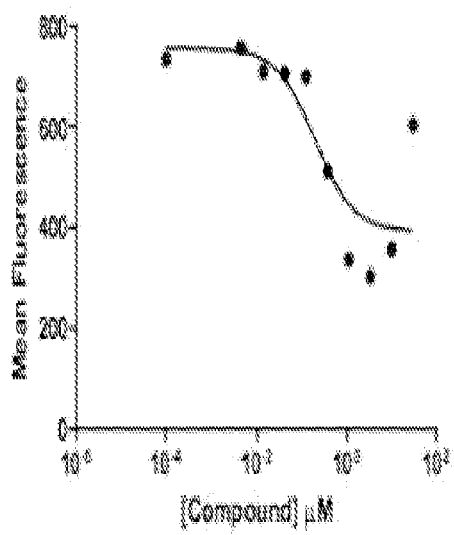

METHODS FOR REDUCING SUPEROXIDE ANIONS IN EUKARYOTIC ORGANISMS

CROSS-REFERENCE TO RELATED APPLICATIONS

This application claims priority to U.S. provisional patent application no. 61/317,056, filed Mar. 24, 2010, U.S. provisional patent No. 61/346,275, filed May 19, 2010, U.S. provisional patent application No. 61/347,992, filed May 25, 2010, and U.S. provisional application No. 61/361,111, filed Jul. 2, 2010, the disclosures of each of which are incorporated herein by reference.

GOVERNMENT FUNDING

This invention was made with government support under grant nos. 1R03 MH087439-01 and 1U54 MH084690-01 awarded by the National Institutes of Health. The government has certain rights in the invention.

BACKGROUND OF THE INVENTION

Superoxide anions (O2-) are a form of reactive oxygen implicated as a causal factor in aging and age-related diseases in humans, including cancer, neurodegenerative disorders, cardiovascular disease and diabetes. Intracellular $O_2^-$ levels are elevated as a consequence of the induction of intracellular growth signaling pathways by mitogenic growth factors or glucose and other carbohydrates. Elevated levels of $O_2^-$ are also an important component of inflammatory responses mediated by the immune system. There is an ongoing and unmet need to provides compositions and methods for prophylaxis and/or therapy via reduction in superoxide anions so that therapies for aging, age-related diseases and/or undesirable inflammation can be provided. The present invention meets these and other needs.

SUMMARY OF THE INVENTION

In the present invention, we demonstrate that caloric restriction (CR) enhances lifespan and helps inhibit age-related diseases by inhibiting growth signaling, which leads to a reduction in intracellular levels of $O_2^-$. In this regard, we show that compounds that mimic the effects of CR are useful therapeutics that would be expected to provide a prophylactic and/or therapeutic benefit against aging and age-related diseases and disorders related to undesirable and/or excessive inflammation. Further, compounds that mimic the effects of CR are also potentially valuable research probes for dissecting the molecular mechanisms underlying the lifespan-enhancing and health-promoting effects of CR.

In one embodiment, the invention provides a method for altering the lifespan of a eukaryotic organism and/or reducing inflammation in the individual by administering to the individual a composition comprising a compound having a structure selected from the group of structures consisting of:

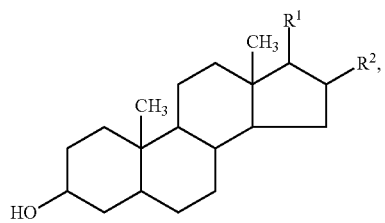

wherein $R^1$ is a hydroxyl group, a carboxylic acid group or an ester group, and
$R^2$ is an alkyl group comprising from 1 carbon to 5 carbons;

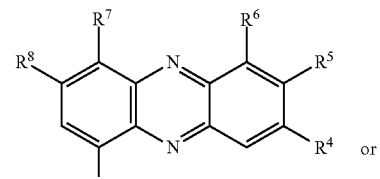

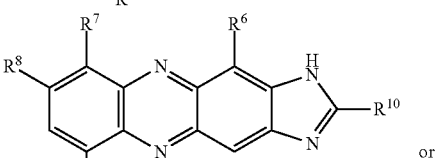

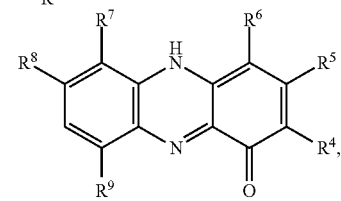

wherein $R^4$ is H or $-NH_2$,
$R^5$ is H or $-NH_2$,
$R^6$ is H, a $-OR^{11}$ group, or an ester group, wherein $R^1$ is a H or an alkyl group,
$R^7$ is H or $NH_2$,
$R^8$ is H, an ethergroup, $-(O)COR^{15}$, wherein $R^{15}$ is a alkyl group, $NR^{16}R^{17}$, wherein $R^{16}$ and $R^{17}$ are independently an alkyl group, or $-NHC(O)R^{18}$, wherein $R^{18}$ is an alkyl group,
$R^9$ is H or an alkyl group, and
$R^{10}$ is H or an alkyl group;

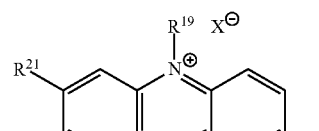

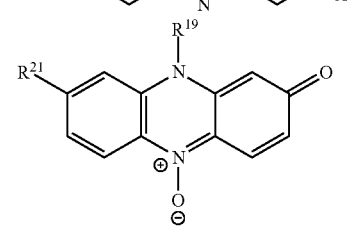

-continued

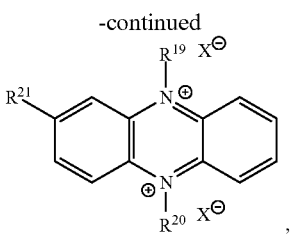

wherein $R^{19}$ is hydrogen, —OH, an alkyl group, and $R^{21}$ is —$NHR^{22}$, wherein $R^{22}$ is an alkyl group, an —$OR^{23}$ group, wherein $R^{23}$ is an alkyl group, or morpholino group, and $X^-$ is a counter-ion;

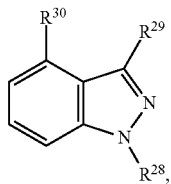

wherein $R^{28}$ is H, an alkyl group, or a phenyl group,
$R^{29}$ is H, a substituted phenyl,
$R^{30}$ is $NHR^{31}$, wherein $R^{31}$ is H or an alkyl group; and

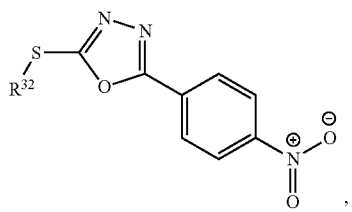

wherein $R^{32}$ is a thioether.

In other aspects, the invention provides pharmaceutical preparations comprising one or more of compounds described above. Also provided is a method of identifying inhibitors of superoxide formation which utilizes a high throughput flow cytometer. This embodiment comprises growing yeast in the presence of a growth media which permits high concentrations of superoxide formation in a microtiter plate at a liquid-air interface in the presence of potential inhibitors and/or control agents.

DESCRIPTION OF THE FIGURES

FIG. 4: Effects of SC medium containing 10% or 2% glucose on cell death in stationary phase. (A) % wild type cells cultured in 10% glucose SC medium stained with propidium iodide (PI) at day 2 of medium depletion. (B) DNA content of wild type cells cultured in 10% or 2% glucose SC medium at day 2 of stationary phase. Dotted line marks cells with a G1 content of DNA. (C-E) Electron micrographs of stationary phase cells cultured in 2% glucose SC medium undergoing apoptosis (C and D) or not undergoing apoptosis (E). (F) Number of particles in 10% glucose SC cultures at day 1 and 3 of medium depletion.

FIG. 10: A tabular summary of yeast strains and genotypes used in the invention.

FIGS. 11-20 provide dose response curves for compounds used in the invention.

DESCRIPTION OF THE INVENTION

Figure 1:
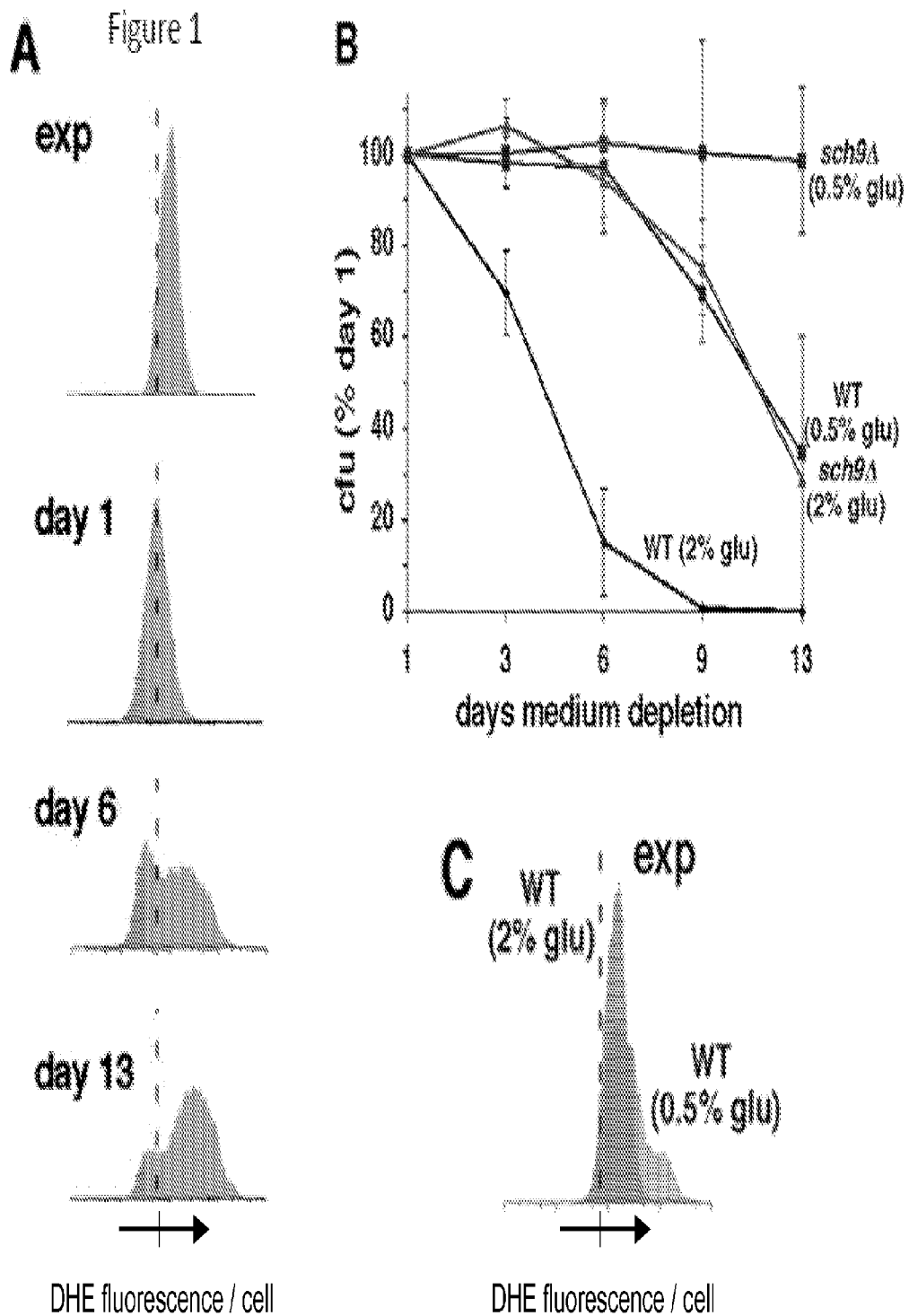
FIG. 1: Inhibition of growth signaling pathways prolongs chronological lifespan (CLS) in concert with reduced O2- and more frequent growth of stationary phase cells in G0/G1. (A) Levels of O2- detected by dihydroethidium (DHE) fluorescence in exponential cultures and stationary phase wild type cells. In this and subsequent figures, dashed vertical line through flow cytometry histograms provides an arbitrarily chosen reference point for comparing related histograms. (B) Effects of caloric restriction and/or inactivation of Sch9p on CLS. (C) Effect of caloric restriction on levels of O2- detected by DHE fluorescence in exponential cultures of wild type cells. (D) Effects of caloric restriction and/or inactivation of Sch9p on levels of O2- detected by DHE fluorescence in stationary phase cells at day 3 of medium depletion. (E) Effects of caloric restriction and/or inactivation of Sch9p on the fraction of stationary phase cells that failed to arrest in G0/G1 as measured by counting cells with visible buds at day 3 of medium depletion. (F) Levels of H2O2 detected in stationary phase wild type and sch9Δ cells by dihydrorhodamine 123 (DHR) fluorescence at day 3. (G) Levels of H2O2 detected by DHR fluorescence and O2- detected by DHE fluorescence in rim15Δ cells at day 3.

In the present invention, we provide data supporting use of compounds as described further herein for mimicking the effects of caloric restriction (CR). We show that mimicking CR results in inhibition of growth signaling and a reduction in intracellular levels of $O_2^-$, which are effects that are expected to enhance lifespan and to be useful for prophylaxis and/or therapy of age-related diseases. Additionally, compounds that mimic the effects of CR are also potentially valuable research probes for dissecting the molecular mechanisms underlying the lifespan-enhancing and health-promoting effects of CR. Thus, the present invention provides compositions and methods that are useful for a variety of purposes.

The compounds for use in the method of the invention were identified in a high throughput small molecule screen based on their ability to reduce basal levels of intracellular $O_2^-$ in stationary phase budding yeast cells by at least three standard deviations from negative controls. This mimics the effects of CR on stationary phase cells, which also causes a reduction in intracellular $O_2^-$ levels in parallel with enhanced longevity as measured by how long stationary phase cells survive. The assay used to identify the compounds is described more fully in the Examples presented herein. The compounds that we have determined to be suitable for use in the invention comprise the following non-limiting embodiments, which in certain cases refer to PubChem identifying numbers. In connection with this, those skilled in the art will recognize that PubChem is database of chemical compounds maintained by the National Center for Biotechnology Information (NCBI), which a component of the National Library of Medicine, which is in turn part of the United States National Institutes of Health (NIH). The structures of each of the compounds associated with the PubChem numbers set forth herein are readily accessible to the public via the PubChem website (pubchem.ncbi.nlm.nih.gov/).

In one embodiment, the compounds have a cyclopentanoperhydrophenanthrene skeleton and have the following structure:

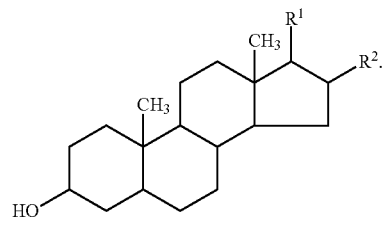

In this embodiment, $R^1$ is a hydroxyl group, a carboxylic acid group or an ester group (e.g., $—OC(O)R^3$, where $R^3$ is H or an alkyl group comprising from 1 to 10 carbons, including all ranges and integer number of carbons therebetween). $R^2$ is an alkyl group comprising from 1 to 5 carbons, including all ranges and integer number of carbons therebetween. The alkyl groups of this embodiment can be substituted (e.g., substituted with a halogen or $—NH_2$) or unsubstituted and branched or linear. A non-limiting example of $R^2$ is $—(CH_2)_3CH_2Cl$. A non-limiting example of $R^3$ is $—CH(NH_2)(CH_2)_3CH_2(NH_3)$. In various embodiments, the compound is any stereoisomer of this structure.

In various embodiments, the compound (identified by PUB CHEM identifier and IUPAC name, and in some cases common name, following in parentheses) is MLS002554375 ((3S,5S,10S,13S,14R,17R)-10,13-dimethyl-2,3,4,5,6,7,8,9,11,12,14,15,16,17-tetradecahydro-1H-cyclopenta[a]phenanthrene-3,17-diol), MLS002554453 ((3R,5S,10S,13S,16R,17S)-16-(3-chloropropyl)-10,13-dimethyl-2,3,4,5,6,7,8,9,11,12,14,15,16,17-tetradecahydro-1H-cyclopenta[a]phenanthrene-3,17-diol, and MLS002554454 (common name: Isoandrosterone; (3R,5S,10S,13S)-3-hydroxy-10,13-dimethyl-1,2,3,4,5,6,7,8,9,11,12,14,15,16-tetradecahydro-cyclopenta[a]phenanthren-17-one.

In an embodiment, the compounds are phenazine compounds. Non-limiting examples of phenazine compounds include phenazine, phenazinium compounds and substituted phenazine or phenazinium compounds. Phenazine compounds of this embodiment have, for example, the following structures:

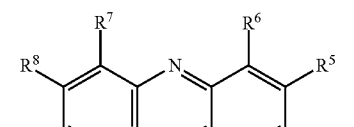

or

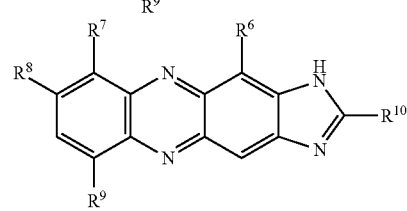

or

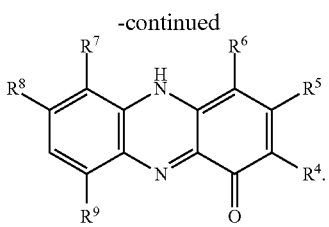

In these phenazine compounds, $R^4$ is H or —$NH_2$; $R^5$ is H or —$NH_2$; $R^6$ is H, a —$OR^{11}$ group, where $R^{11}$ is a H or an alkyl group, an ester group (e.g., —(O)$COR^{12}$, where $R^{12}$ is a alkyl group or a morpholino group), or an amide group (e.g., —(O)$CONHR^{13}$, where $R^{13}$ is an alkyl group); $R^7$ is H, $NH_2$; $R^8$ is H, an ether group (e.g., —$OR^{14}$, where $R^{14}$ is H or an alkyl group), —(O)$COR^{15}$, where $R^{15}$ is a alkyl group, $NR^{16}R^{17}$, where $R^{16}$ and $R^{17}$ are independently an alkyl group, or —NHC(O)$R^{18}$, where $R^{18}$ is an alkyl group; $R^9$ is H or an alkyl group; and $R^{10}$ is H or an alkyl group.

In various embodiments, the phenazine compounds (identified by PUB CHEM identifier and IUPAC name following in parentheses) are MLS000700045 (1H-imidazo[4,5-b]phenazine, MLS001049309 (2-(trifluoromethyl)-1H-imidazo[4,5-b]phenazine), MLS001044416 (phenazine-2,3-diamine), MLS000584128 (phenazine), MLS000863638 (methyl 6-(1-hydroxyethyl)phenazine-1-carboxylate), MLS001044341 (2-methoxyphenazin-1-amine), MLS001044346 (N-methylphenazine-1-carboxamide), MLS001173415 (propan-2-yl phenazine-2-carboxylate), MLS000418506 (N-phenazin-2-ylbenzamide), MLS000737174 (5H-phenazin-1-one), MLS001044337 (morpholin-4-yl(phenazin-1-yl)methanone), MLS000768124 (2-methoxyphenazine), MLS000756830 (1-methoxy-7,8-dimethylphenazine), MLS001048992 (2-methoxyphenazine), MLS000595212 (N,N-diethylphenazine-2-carboxamide), MLS001003683 (1,8-dimethoxyphenazine), and MLS001044354 (N-phenazin-2-ylacetamide).

Phenazinium compounds of this embodiment have, for example, the following structures:

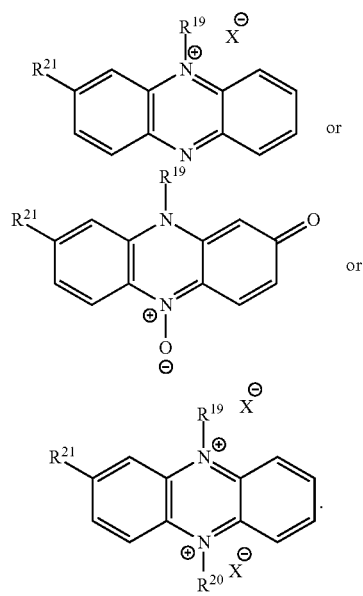

In these phenazinium compounds, $R^{19}$ is hydrogen, —OH, an alkyl group; and $R^{21}$ is —$NHR^{22}$, where $R^{22}$ is an alkyl group, an —$OR^{23}$ group, where $R^{23}$ is an alkyl group, a morpholino group; and $X^-$ is a counter-ion such as, for example, perchlorate. The alkyl groups of this embodiment comprise from 1 to 5 carbons, including all ranges and integer number of carbons therebetween. The alkyl groups can be substituted (e.g., halogen, —OH, —$NH_2$, and the like) or unsubstituted, and branched or linear. Non-limiting examples of alkyl groups are, —$CH_3$, —$CH(CH_3)_2$, perfluorinated alkyl groups (e.g., trifluoromethyl), —$CH(CH_3)OH$, and —$CH_2CH_2OH$.

In various embodiments, the phenazinium compounds (identified by PUB CHEM identifier and IUPAC name following in parentheses) are MLS001164912 (N,10-dimethylphenazin-10-ium-2-amine perchlorate), MLS000768911 (2-(3-morpholin-4-ylphenazin-5-ium-5-yl)ethanolperchlorate), MLS001208198 (10-hydroxy-5-oxidophenazin-5-ium-2-one), MLS002638803 (2-methoxy-10-oxidophenazin-10-ium), and MLS001164888 (2-[(10-methylphenazin-10-ium-2-yl)amino]ethanol perchlorate).

In an embodiment, the compounds are pyrimidine compounds. Non-limiting examples of pyrimidine compounds include pyrimidine and substituted pyrimidine compounds. Pyrimidine compounds of this embodiment have, for example, the following structure:

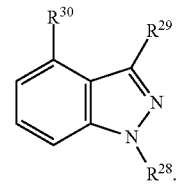

In this embodiment, $R^{28}$ is H, an alkyl group, or a phenyl group; $R^{29}$ is H, a substituted phenyl; $R^{30}$ is $NHR^{31}$ where $R^{31}$ is H or an alkyl group. The alkyl groups of this embodiment comprise from 1 to 5 carbons, including all ranges and integer number of carbons there between. The alkyl groups can be substituted or unsubstituted, and branched or linear. Non-limiting examples of alkyl groups are —$CH_3$ and —$C(CH_3)_3$. The phenyl groups of this embodiment can be substituted (e.g., substituted with halogen or alkyl groups) or unsubstituted. Non-limiting examples of phenyl groups are phenyl, 4-methyl phenyl, 4-chlorophenyl, 4-fluorophenyl and the like.

In various embodiments, the pyramidine compounds (identified by PUB CHEM identifier and IUPAC name following in parentheses) are MLS000100785 (N-tert-butyl-1-phenylpyrazolo[3,4-d]pyrimidin-4-amine), MLS000326584 (1-tert-butyl-3-(4-fluorophenyl)pyrazolo[3,4-d]pyrimidin-4-amine), MLS000326622 (1-tert-butyl-3-(4-chlorophenyl)pyrazolo[3,4-d]pyrimidin-4-amine), and MLS000326642 (1-tert-butyl-3-(4-methylphenyl)pyrazolo[3,4-d]pyrimidin-4-amine). In one embodiment, the compounds are pyramidine compounds with the proviso that MLS000326622 (1-tert-butyl-3-(4-chlorophenyl)pyrazolo[3,4-d]pyrimidin-4-amine) is not a pyrimidine compound.

In an embodiment, the compounds are oxadiazole compounds. Non-limiting examples of oxadiazole compounds include substituted pyrimidine compounds. Oxadiazole compounds of this embodiment have, for example, the following structure:

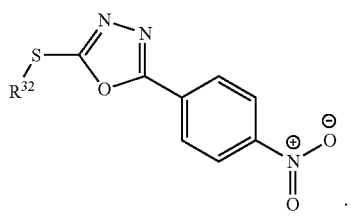

In this embodiment, $R^{32}$ is a thioether (e.g., —$SR^{33}$, where $R^{33}$ is an alkyl group). The alkyl groups of this embodiment comprise from 1 to 5 carbons, including all ranges and integer number of carbons therebetween. The alkyl groups can be substituted or unsubstituted (e.g., substituted with an alkene (—C═C—) or alkyne group (—C≡C—), and branched or linear. Non-limiting examples of alkyl groups are —$CH_2C$═C and —$CH_2C$≡CH.

In various embodiments, the oxadiazole compounds (identified by PUB CHEM identifier and IUPAC name and common name following in parentheses) are MLS000663774 (2-(4-nitrophenyl)-5-prop-2-ynylsulfanyl-1,3,4-oxadiazole), MLS000662516 (2-(4-nitrophenyl)-5-prop-2-enylsulfanyl-1,3,4-oxadiazole), and MLS000855890 (2-methylsulfanyl-5-(4-nitrophenyl)-1,3,4-oxadiazole).

In various embodiments, the compounds of the present invention (identified by PUB CHEM identifier and IUPAC name, and in some cases common name, following in parentheses) are MLS002320508 (common name: Okadaic acid; (2R)-3-[(4S,10S)-4-[(E)-4-[(2S,2'R,4aS,6R,8aR)-4-hydroxy-2-[1-hydroxy-3-[(10S)-9-methyl-5,11-dioxaspiro[5.5]undecan-10-yl]butyl]-3-methylidenespiro[4a,7,8,8a-tetrahydro-4H-pyran[3,2-b]pyran-6,5'-oxolane]-2'-yl]but-3-en-2-yl]-7-hydroxy-2-methyl-5,11-dioxaspiro[5.5]undec-1-en-10-yl]-2-hydroxy-2-methylpropanoic acid), MLS000554700 (6-Methoxy-1,3-dimethyl-1H-benzo[de]cinnoline), MLS000033501 (8-methoxy-5-methyl-3-methylsulfanyl-[1,2,4]triazino[5,6-b]indole), MLS000779260 (2-[1-(2-hydroxyanilino)propylidene]-5-phenylcyclohexane-1,3-dione), MLS000121367) ((E)-3-phenyl-N—[[(2-thiophen-2-ylacetyl)amino]carbamothioyl]prop-2-enamide, and MLS001176565 (5,6-dimethyl-N-(1-pyridin-2-ylethylideneamino)thieno[2,3-d]pyrimidin-4-amine).

In various embodiments, modification of the compounds described herein, for example in the specific embodiments above, which result in derivatives of the compounds that maintain activity are intended to fall within the scope of the present invention.

Specific examples of compounds that exhibited dose dependency in re-screening via a high-throughput method more fully described in the Examples herein include the following compounds which are identified by their respective PubChem numbers: MLS002320508, MLS000554700, MLS002554375, MLS002554453, MLS002554454, MLS002554450, MLS000700045, MLS001049309, MLS001044416, MLS001164912, MLS000584128, MLS000863638, MLS000768911, MLS001208198, MLS001044341, MLS001044346, MLS001173415, MLS000418506, MLS000033501, MLS000100785, MLS000326584, MLS000326622, MLS000326642, MLS000663774, MLS000662516, MLS000779260, MLS000121367; MLS000737174, MLS002638803, MLS001044337, MLS000768124, MLS000756830, MLS001048992, MLS001164888, MLS002153505, MLS000595212, MLS001003683, MLS000855890, MLS001044354, and MLS001176565.

Screening of these compounds performed as set forth in Example 2 yielded the data presented in FIGS. 11-20 and we confirmed that these compounds as having dose dependency (DD) using such methods. Each of these compounds, and each member of each class of compounds disclosed herein is referred to collectively as "DD compounds" and each as a "DD compound."

The $O_2^-$-reducing properties of the DD compounds indicate they function as CR mimetics in eukaryotic cells, and thus can be expected to be efficacious in the method of the invention, as for example, agents suitable for prophylaxis and/or therapy of aging and/or age-related diseases, as well as for molecular probes for dissecting CR mechanisms.

In one embodiment, the invention comprises contacting a biological substance with a DD compound so that the level of $O_2^-$ in the biological substance is reduced. The biological substance can be any biological substance that comprises cells, including but not necessarily limited to biological substances selected from tissues, biological fluids, organs, etc.

In one embodiment, the invention comprises administering a composition comprising at least one DD compound to an individual so that the level of $O_2^-$ in the individual is reduced. The level of $O_2^-$ in the individual may be reduced in cells, tissues, biological fluids, etc., of the individual. In one embodiment, the invention comprises administering a composition comprising at least one DD compound to an individual for prophylaxis and/or therapy of a disorder. The disorder can be any disorder that is caused by or is positively correlated with an abnormal oxidative state. In one embodiment, the disorder is caused by and/or is correlated with elevated levels of $O_2^-$. In one embodiment, the elevated levels of $O_2^-$ comprise elevated intracellular levels of $O_2^-$.

In one embodiment, the individual to whom a composition comprising at least one DD compounds is administered is an individual who is at risk for, is suspected of having, or is diagnosed with a disorder that is caused by and/or is correlated with elevated levels of $O_2^-$.

In one embodiment, the individual to whom a composition comprising at least one DD compound is administered is an individual who is at risk for, is suspected of having, or is diagnosed with a disorder that is an age-related disorder.

In one embodiment, the invention comprises a method for prophylaxis and/or therapy of inflammation in an individual. The inflammation can be chronic or acute. The method comprises administering to the individual a composition comprising one or more of the DD compounds disclosed herein, such that inflammation in the individual is inhibited and/or reduced subsequent to administration of the composition. A reduction in inflammation can be evidenced by a reduction in the production of any of various well known markers of inflammation which include but are not necessarily limited to a reduction in cytokines typically associated with inflammation, interleukins, TNFα, or MCP-1.

In one embodiment, the individual to whom a composition comprising one or more of the compounds disclosed herein is administered is an individual who is at risk for, is suspected of having, or is diagnosed with a disorder that is caused by and/or is positively correlated with abnormal and/or undesirable inflammation. In one embodiment, the inflammation is positively correlated with an age-related disease.

In one embodiment, the compositions and methods of the invention can inhibit growth signaling in a cell or in a plurality of cells, such as in a multicellular eukaryotic organism. In one embodiment, the invention facilitates an inhibition of growth signaling that would otherwise promotes chronological aging in such an organism.

In one embodiment, performance of the method of the invention can affect the lifespan of one or more eukaryotic cells. The eukaryotic cell can be a cultured cell, such as a tissue cell culture, or the cell can be one of many cells in, for example, a tissue, or an organ, or a biological system. Thus, the lifespan of a tissue or an organ, for example, a tissue or an organ that is intended for transplantation, can be altered using the method of the invention. Lifespan can include the number of times a cell or cell population can divide (replicative lifespan), or the length of time a cell or organism survives before dying (chronological lifespoan). In preferred embodiments, the lifespan of the multicellular eukaryotic organism is extended, relative to a similar multicellular eukaryotic organism that does not receive a composition of the invention. Thus, in various embodiments, the invention provides for reducing inflammation in and/or affecting the lifespan of a multicellular eukaryotic organism, such as a mammal. In one embodiment, the mammal is a human.

In one embodiment, performance of the present invention can cause mammalian cells that are contacted with a composition comprising a compound of the invention to become quiescent. In an embodiment, prior to being becoming quiescent, the mammalian cells are senescent. Thus, the invention can be used to induce mammalian cells to become quiescent.

In one embodiment, the individual to whom a composition comprising at least one DD compound is an individual who is at risk for, is suspected of having, or is diagnosed with a cancer. The cancer may be one that affects any tissue in the individual. The cancer may thus comprise a blood cancer, and/or a solid tumor(s), and/or metastatic foci, or any other form of cellular and/or tissue and/or organ-based malignancy.

In one embodiment, the individual to whom a composition comprising at least one DD compound is administered is an individual who is at risk for, is suspected of having, or is diagnosed with a disorder that is caused by and/or is positively correlated with abnormal and/or undesirable inflammation of one or more biological substances in the individual. The abnormal and/or undesirable inflammation can be due to dis-regulated immunological responses in the individual, which dis-regulated immunological responses can be caused by any factor, examples of which include but are not limited to autoimmune diseases, infections, cancers, diabetes, ischemia, trauma, neurological disorders, neuromuscular disorders, or any other cause of abnormal and/or undesirable inflammation. Each of these disorders may also be suitable for therapy and/or prophylaxis using the method of the invention even if abnormal and/or undesirable inflammation is not present in the individual or in the particular tissue affected by the disorder.

In one embodiment, the individual to whom a composition comprising at least one DD compound is administered is an individual who is at risk for, is suspected of having, or is diagnosed with a disorder that affects the weight and/or body mass index of the individual. Thus, the individual may be at risk for obesity, or the individual may be obese.

In one embodiment, the invention provides a method for determining whether an individual is a candidate for therapy and/or prophylaxis of a disorder comprising using at least one DD compound and according to the methods for prophylaxis/therapy as described herein. The method comprises determining whether the individual is at risk for, is suspected of having, or is diagnosed with any disorder as described supra, wherein identifying the individual as such is indicative that the individual is a candidate for receiving a therapeutic and/or prophylactic administration(s) of a composition comprising at least one DD compound. The determination can be performed on a biological sample obtained from the individual and assaying the sample or preparations derived therefrom for the presence of elevated levels of $O_2^-$. The method further comprises fixing the determination that the individual is such a candidate in a tangible medium. The method further comprises communicating and/or transporting the determination, whether or not fixed in a tangible medium, to a healthcare provider. Thus, the method further comprises developing a treatment protocol for an individual determined to be a candidate for prophylaxis and/or therapy as described herein.

The compositions comprising at least one DD compound can be formulated into pharmaceutical preparations using standard methods and reagents, excipients, and the like. Likewise, given the benefit of the present disclosure, dosing parameters can be determined by the skilled artisan, taking into account such factors as the size, sex and age of the individual, the chemical composition of the particular compound(s) used in the method, and other factors that can be determined using ordinary techniques.

Compositions comprising at least one DD compound can be administered to the individual using any suitable route and/or method of administration. The administrations can be performed in conjunction with any other conventional treatment modality for the particular disorder under consideration for the individual. For example, in the case of cancer, the method of the invention can be performed concurrently, before or after conventional chemotherapies, surgical interventions, and the like.

The following examples are provided to illustrate the invention and are not to be considered as limiting in any way.

EXAMPLE 1

This Example demonstrates that caloric restriction (CR) enhances lifespan and helps inhibit age-related diseases by inhibiting growth signaling, which leads to a reduction in intracellular levels of $O_2^-$. In particular, we show that in *Saccharomyces cerevisiae*, alterations in growth signaling pathways impact levels of superoxide anions, promote chronological aging and inhibit growth arrest of stationary phase cells in G0/G1. Yeast strains and their genotypes used in this analysis are shown in FIG. 10. Factors that decrease intracellular superoxide anions in parallel with enhanced longevity and more efficient G0/G1 arrest include genetic inactivation of growth signaling pathways that inhibit Rim15p, which activates oxidative stress responses, and downregulation of these pathways by caloric restriction. Caloric restriction also reduces superoxide anions independently of Rim15p by elevating levels of H2O2, which activates superoxide dismutases. In contrast, high glucose or mutations that activate growth signaling accelerate chronological aging in parallel with increased superoxide anions and reduced efficiency of stationary phase G0/G1 arrest. High glucose also activates DNA damage responses and preferentially kills stationary phase cells that fail to arrest growth in G0/G1. These findings indicate that growth signaling promotes chronological aging in eukaryotic cells by elevating superoxide anions that inhibit quiescence and induce DNA replication stress. A similar mechanism likely contributes to aging and age-related diseases in complex eukaryotes, and thus, compounds that can reduce superoxide anions in complex eukaryotic would be expected to alleviate age-related diseases and reduce inflammation that is also associated with superoxide anion production.

The following materials and methods were used to obtain the data presented in this Example. To assess CLS 50 ml cultures were inoculated with 1% (v/v) of a fresh overnight culture in either SC or YPD. SC was supplemented using known techniques. In experiments that employed media that initially contained 10% glucose, control 2% glucose cultures also contained 8% sorbitol to maintain equivalent osmolarity. Determination of chronological life span, fraction of budded cells, flow cytometry measurements of DNA content and measurements of dihydroethidium (DHE) and dihydrorhodamine 123 (DHR) were used according to standard methods. N-acetylcysteine (NAC) and glutathione (GSH) were dissolved in growth medium, filter sterilized and added to cultures from 100 mM (NAC) or 250 mM (GSH) stocks at the start of experiments. Propidium iodide (PI) was used to assess viability of cells by mixing a 2 μl of cells with an equal volume of 1 mM PI on a microscope slide and examining the slide with a fluorescence microscope equipped with a Texas Red filter. Non-fluorescent cells were scored as intact (live) and fluorescent cells were scored as dead. The total number of cells in cultures was determined by particle counts using a Petroff Hauser counting chamber. Samples for transmission electron microscopy were prepared using standard methods. Briefly, cells cultured at 30° C. in YPD medium for 3 to 5 days were harvested by gentle centrifugation, washed in phosphate buffered saline (PBS) (pH=7.2), resuspended in 2.5% (v/v) glutaraldehyde in PBS and fixed for 40 min at room temperature. Cells were further fixed by 2% freshly prepared potassium permanganate in water for 1 hour at room temperature. Fixed cells were dehydrated with 30%, 50%, 75%, 85%, 95%, and 100% ethanol. Cells were transitioned with propylene oxide, infiltrated in Spurr resin (Electron Microscopy Sciences, PA). Resin was polymerized at 65° C. overnight in the oven. 60 nm ultrathin sections were cut with a diamond knife, stained with 2% uranyl acetate and lead citrate and examined using a Hitachi H-7000 electron microscope, equipped with a 4K×4K cooled CCD digital camera (Gatan, Inc., CA). Values presented in graphs that contain error bars represent means and standard deviations from three or more independent experiments. Other results are representative of at least three independent experiments. Statistical analyses were performed using Student's t-test. $P<0.05$ was considered statistically significant.

Figure 7:
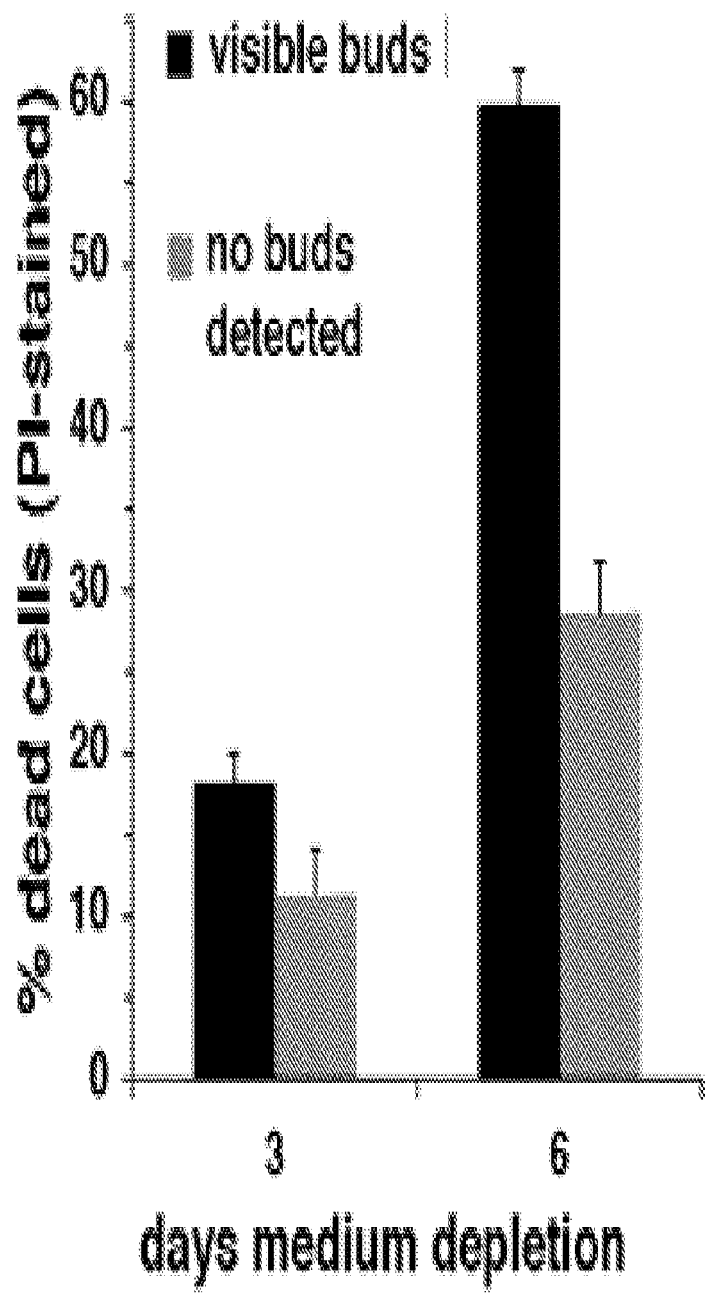
FIG. 7: Graphical representation of an identification of dead or dying cells in stationary phase by stating with the membrane-impermeable dye propidium idodide.

We show that caloric restriction or inactivation of growth signaling pathways reduces superoxide anions in stationary phase cells and enhances G0/G1 arrest. In particular, chronological lifespan experiments require the establishment of exponentially dividing cultures of cells that eventually deplete nutrients from the medium, leading to entry into a non-dividing stationary phase state a few days later. Compared to exponential cultures, intra-cellular levels of O2- detected by the fluorescent probe dihydroethidium (DHE), which can detect superoxide, initially declined during the few days of experiments but then gradually accumulated with time in stationary phase (FIG. 1A). The chronological age-dependent accumulation of O2- occurred in parallel with loss of reproductive capacity as measured by colony-forming units (FIG. 1B; "WT 2% glu"). Both the accumulation of O2- and loss of reproductive capacity in stationary phase cells were accompanied by an increase in cell death as measured by uptake of the membrane-impermeable DNA stain propidium iodide (PI) (FIG. 7), which does not stain viable cells with intact membranes. The rate of cell death was accelerated in cells with visible buds that failed to exit the cell cycle in stationary phase compared to cells without visible buds (FIG. 7).

Figure 8:
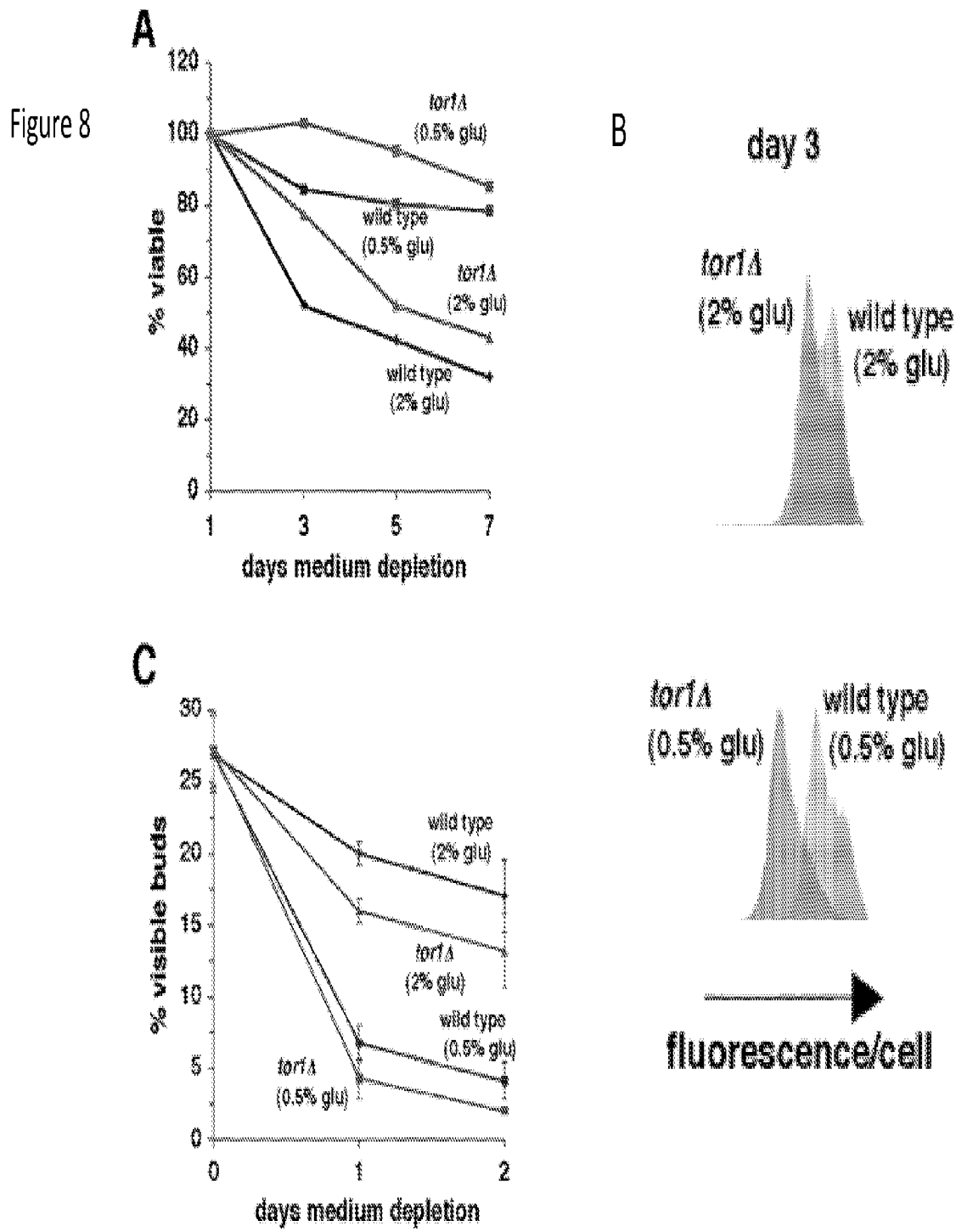
FIG. 8: Graphical representation of data obtained by analyzing effects of inactivation of Tor1 and/or caloric restriction on CLS (A) levels of superoxide anions detected by DHE (B) and fraction of cells that fail to arrest in G0/G0 stationary phase (C).
Figure 9:
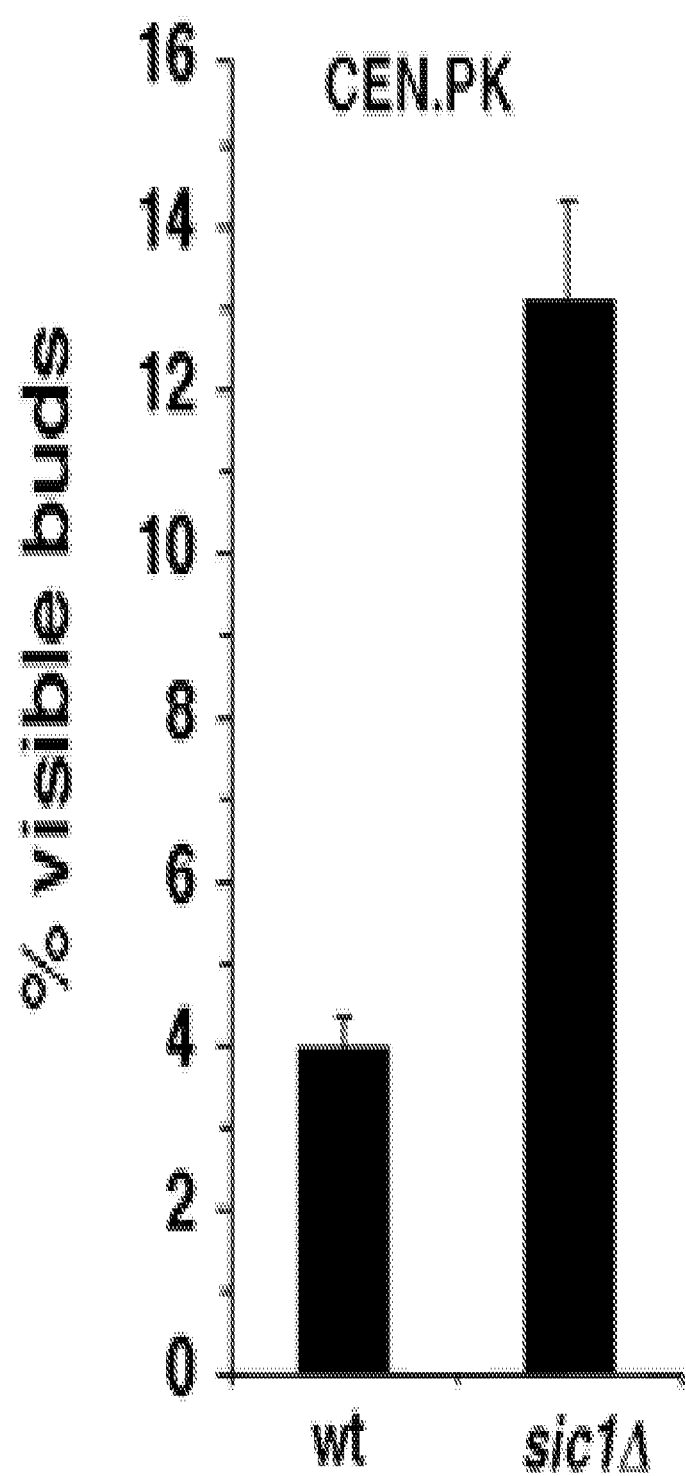
FIG. 9: Graphical representation of data showing that inactivation of Sic1 inhibits growth arrest of stationary phase cells in G0/B2 in the CEN.PK background.
Figure 16:
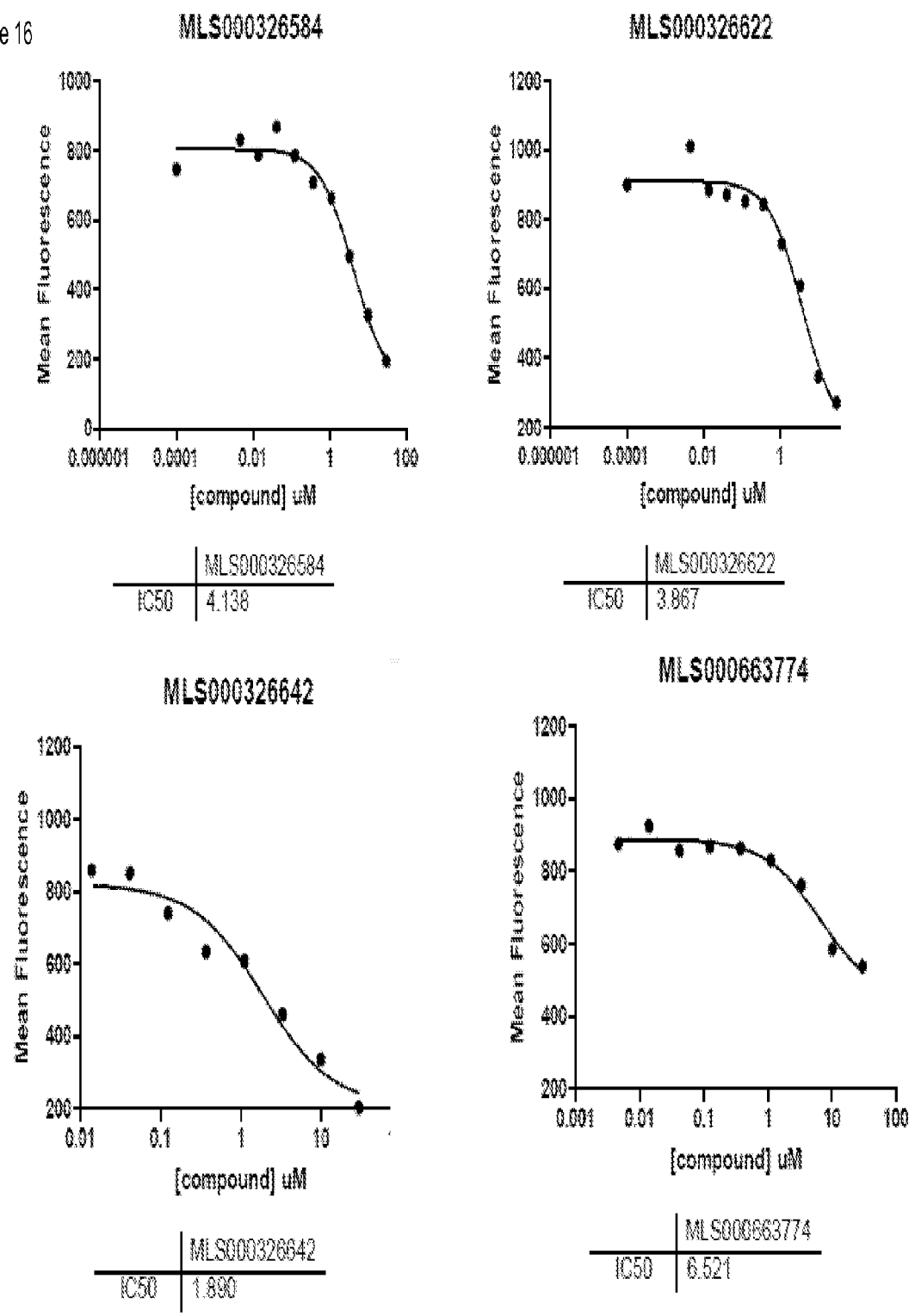
Figure 19:
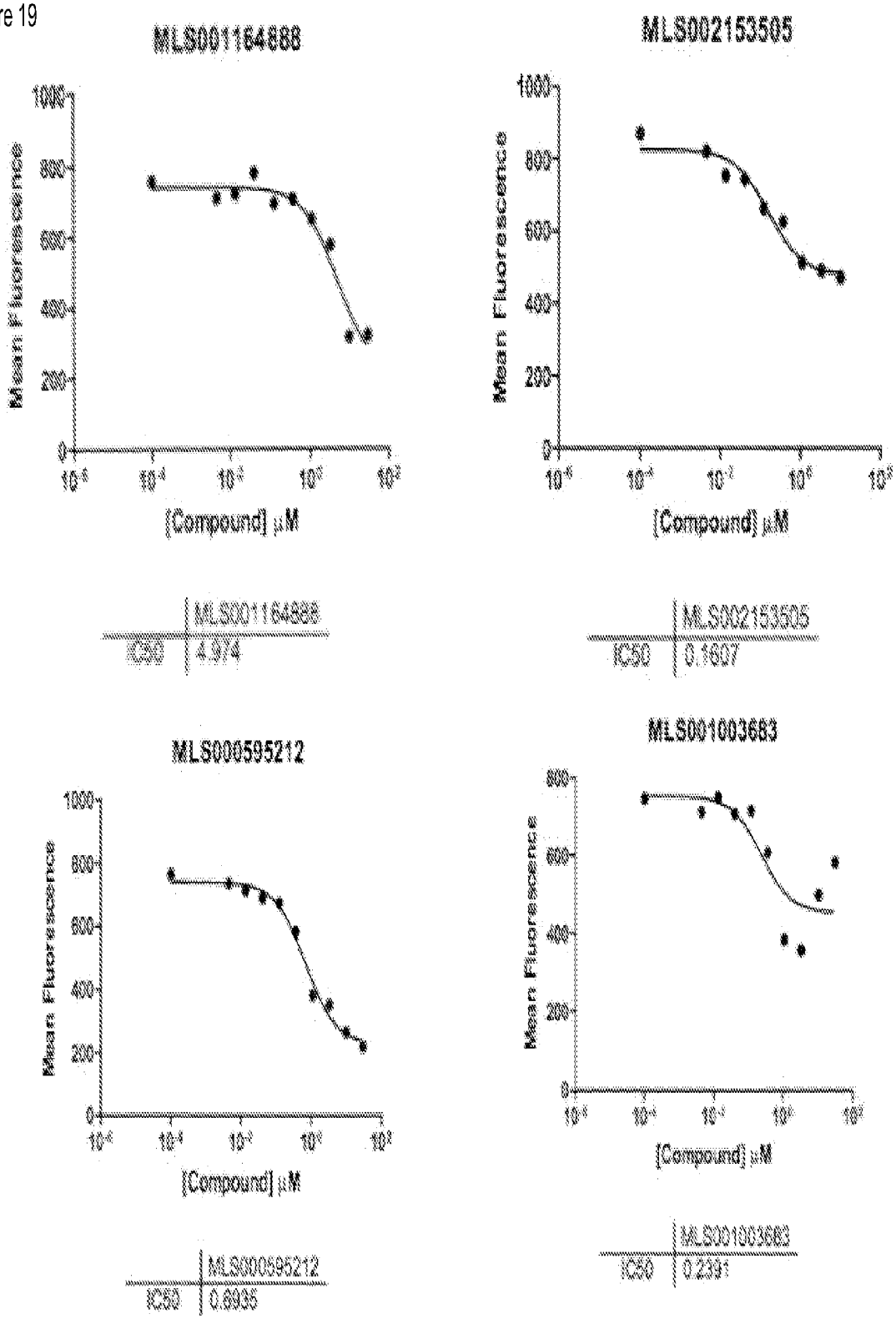
Figure 20:
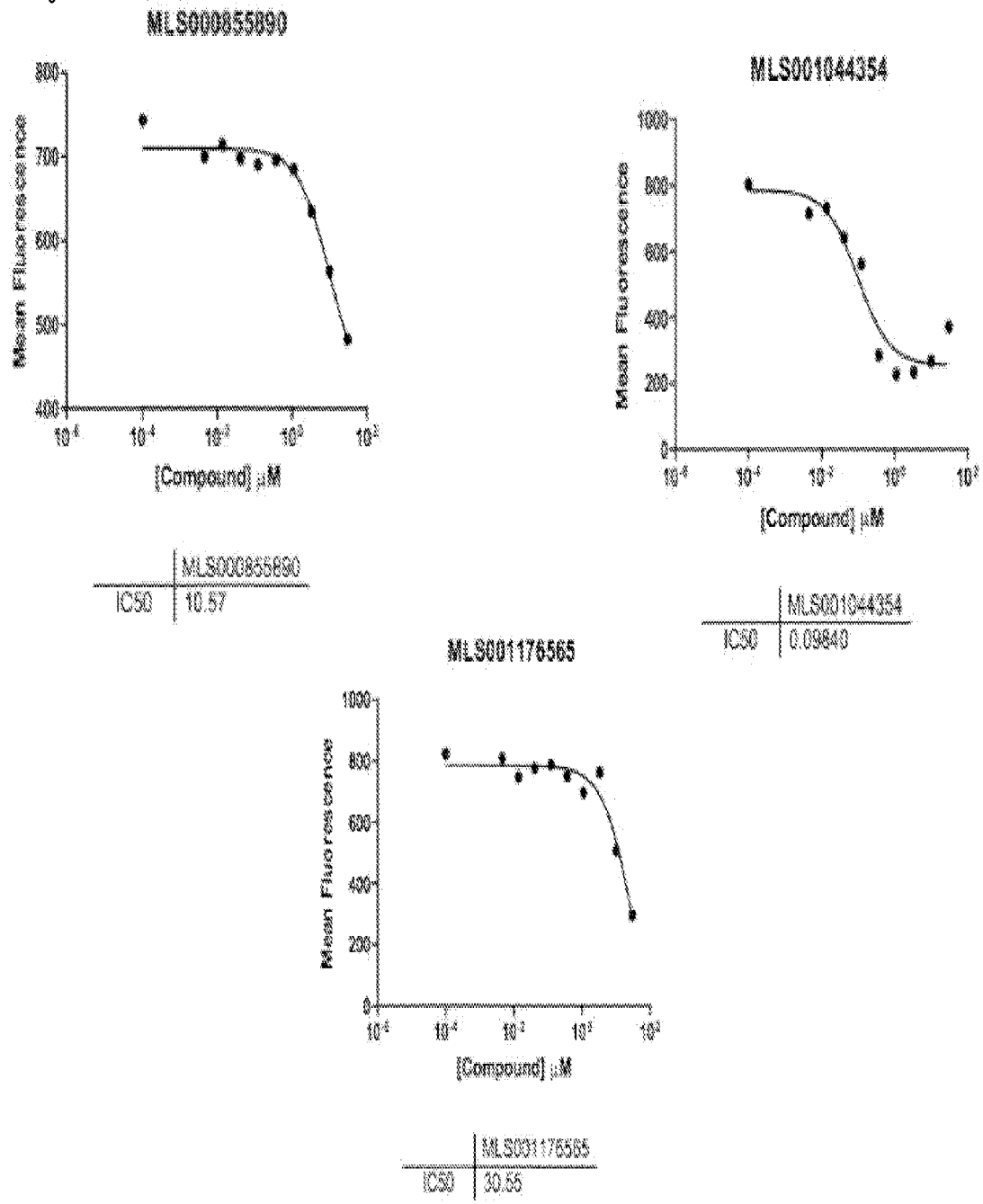

CR by reducing the initial concentration of glucose in growth medium from 2% to 0.5% extended the CLS of wild type cells (FIG. 1B). Although CR initially increased O2- in exponential cultures at the start of CLS experiments (FIG. 1C), it led to a reduction in O2- in stationary phase cultures three days later (FIG. 1D; compare "WT 0.5% glu" with "WT 2% glu"). This decrease was detected in association with a decrease in the fraction of cells that failed to arrest in G0/G1 as indicated by visible buds (FIG. 1E). In the absence of CR, CLS was lengthened to a similar extent (compared to CR) in a strain from which the SCH9 gene had been deleted, and CR extended the CLS of sch9Δ cells even further (FIG. 1B). Similar to the effects of CR, the CLS-extending effects of inactivating Sch9p in 2% glucose medium were also accompanied by a decrease in O2-, and inactivation of Sch9p decreased levels of O2- in calorie-restricted cells even further (FIG. 1D). Inactivation of the superoxide dismutase Sch9p also led to a decrease in the fraction of stationary phase cells that failed to arrest growth in G0/G1 as was reported earlier [13], and this fraction was reduced further by CR of sch9Δ cells (FIG. 1E). Similar quantitative effects on efficiency of G0/G1 arrest in stationary phase in parallel with changes in CLS and O2- were observed in medium containing 2% glucose or 0.5% glucose in cells from which TOR1 had been deleted (FIG. 8). Culturing cells in rich medium (YPD) rather than defined medium (SC), which also promotes more frequent growth arrest of stationary phase cells in G0/G1 also reduced levels of O2-compared to cells cultured in SC (FIG. 9 Figure).

Growth signaling pathways that depend on Sch9p, Tor1p and Ras2p converge on inhibition of Rim15p kinase activity that activates Sod2p and other stress responses, which are induced when these growth signaling pathways are genetically ablated or attenuated by CR. Sod1p and Sod2p activity are also induced by H2O2 that accumulates to higher levels in calorie-restricted cells or when catalases have been inactivated. Intracellular levels of H2O2 detected with the fluorescent probe dihydrorhodamine 123 were slightly reduced in stationary phase sch9Δ compared to wild type cells (FIG. 1F; "DHR"). Therefore, unlike CR, inactivation of Sch9 does not reduce levels of O2- by inducing elevated levels of H2O2 that activate SODs. Moreover, CR increased H2O2 and reduced O2- levels in stationary phase rim15Δ cells (FIG. 1G), similar to its effects in wild type cells. Thus, the reduction in O2- levels detected in calorie-restricted cells reflects both Rim15p-dependent effects downstream of reduced signaling by Sch9p, Tor1p and Ras2p that do not depend on increased H2O2, as well as Rim15p-independent effects related to H2O2 induction of SODs. Together, these findings reveal the existence of a quantitative relationship between CLS extension, reduction in intracellular levels of O2- by Rim15p-dependent and -independent mechanisms and more efficient growth arrest of stationary phase cells in G0/G1 when growth signaling is inhibited.

Figure 2:
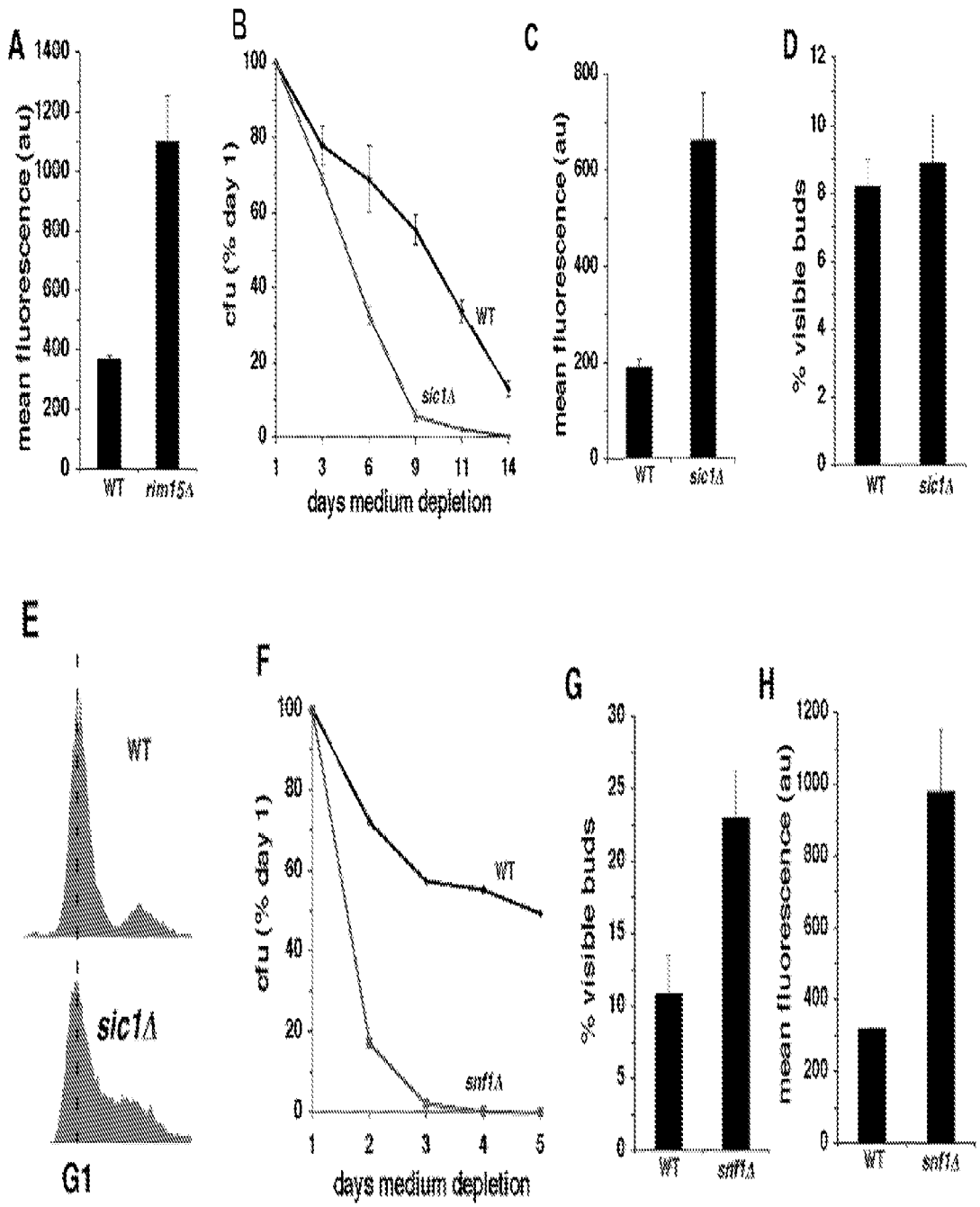
FIG. 2: Constitutive activation of growth signaling pathways shortens CLS in concert with increased O2- and less frequent growth of stationary phase cells in G0/G1. (A) Levels of O2- detected by DHE fluorescence in wild type and rim15Δ cells at day 3 of medium depletion. (B) CLS of wild type and sic1Δ cells. (C-D) Levels of DHE fluorescence (C) and fraction of cells with visible buds (D) in wild type and sic1Δ cells. Measurements depicted in panels C and D were made at day 3 of medium depletion. E. DNA content of wild type and sic1Δ cells at day 3 of medium depletion. (F-H) Effects of inactivating Snf1p on CLS (F), fraction of cells with visible buds (G) and levels of O2- detected by DHE fluorescence. (H) Measurements depicted in panels G and H were made at day 3 of medium depletion.

We also show that constitutive activation of growth signaling elevates superoxide anions and inhibits stationary phase G0/G1 arrest. In particular, in mammals, sustained mitogenic signaling by RAS, AKT and other oncogenes increases levels of O2- and other forms of ROS and induces replication stress in cells that growth arrest in S phase instead of G0/G1 during differentiation. Similar increases in O2- and a reduced frequency of stationary phase growth arrest in G0/G1 phase have been described for budding yeast cells expressing constitutively active Ras2p. As noted above, RAS- and AKT-related path-ways that signal growth in response to nutrients in budding yeast converge on inhibition of Rim15p kinase activity. In addition to exhibiting a shorter CLS, rim15Δ cells fail to arrest in G0/G1 when they enter stationary phase. Stationary phase rim15Δ cells also exhibit higher levels of O2- compared to wild type cells (FIG. 2A)

The mammalian cyclin-dependent kinase inhibitor p27 blocks entry into S phase when mitogenic growth signaling is downregulated in mammalian cells. Sic1p, the budding yeast homologue of p27, similarly inhibits entry of budding yeast cells into S phase when they enter into a nutrient depletion-induced stationary phase growth arrest. Inactivation of Sic1p shortens CLS (FIG. 2B). Similar to the effects of the constitutively active Ras2 or deletion of RIM15, the shorter CLS of sic1Δ cells is accompanied by increased O2- (FIG. 2C). Although in this strain background (W303), deletion of SIC1 did not increase the number of cells with visible buds (FIG. 2D), budding is uncoupled from DNA replication in sic1Δ cells in some genetic backgrounds. Measurements of DNA content by flow cytometry confirmed that a large fraction of stationary phase W303 sic1Δ cells were growth-arrested in S phase, despite a low frequency of buds (FIG. 2E). Uncoupling of budding from DNA replication was not observed, however, in sic1Δ cells in a different genetic background (CEN.PK). sic1Δ cells in this background arrested growth in stationary phase with a substantial increase in the fraction of cells with visible buds (FIG. 9).

Snf1p is a conserved AMP kinase that regulates budding yeast metabolism in response to glucose. In mammals, AMPK inhibits mTOR signaling and is required for a "metabolic checkpoint" that drives cells into G1 in response to reduced glucose concentrations, similar to the more frequent stationary phase growth arrest in G0/G1 imposed by CR during nutrient depletion of budding yeast cells. In addition to exhibiting a shorter CLS compared to wild type cells (FIG. 2F), stationary phase snf1Δ cells also arrested in G0/G1 less frequently (FIG. 2G) and exhibited elevated levels of O2- (FIG. 2H). These findings establish a strong correlation between enhanced growth signaling, increased intracellular levels of O2- and less efficient G0/G1 arrest in stationary phase related to glucose metabolism.

We also show that enhanced growth signaling by high glucose shortens CLS in parallel with increased superoxide anions, less efficient G0/G1 arrest and increased DNA damage in stationary phase cells. In this regard, high glucose is known to accelerate aging in *C. elegans* and hyperglycemia and/or excess calorie intake are risk factors for a number of age-related diseases. High glucose activates AKT in mammalian cells, and similar to enhanced mitogenic signaling by oncogenes, increased growth signaling by elevated levels of glucose promotes senescence in parallel with DNA damage and increased ROS. To determine whether growth signaling by high glucose might trigger related events and accelerate chronological aging in budding yeast, we examined the effects of increasing the concentration of glucose in medium to 10% from the standard 2% (in these experiments, 2% glucose medium also contained 8% sorbitol, a non-metabolized sugar, in order to maintain equivalent osmolarity). Culturing cells in SC medium containing 10% glucose shortened CLS compared to CLS in medium containing 2% glucose (FIG. 3A). The shorter CLS of 10% glucose SC cultures is likely accompanied by DNA damage and/or DNA replication stress, because loss of reproductive capacity was dramatically reduced in cells harboring mutations in the DNA damage/DNA replication stress response proteins Mec1p or Rad53p (FIG. 3B). Cells cultured in 10% glucose SC medium also exhibited increased levels of intracellular O2- (FIG. 3C). This increase occurred in parallel with a reduction in intracellular levels of H2O2 in 10% glucose compared to 2% glucose cultures (FIG. 3D). Since levels of H2O2 are also increased in 0.5% compared to 2% glucose cultures, this suggests that glucose inhibits the accumulation of H2O2 in stationary phase cells in a dose-dependent fashion. The shorter CLS and increased O2- detected in 10% compared to 2% glucose SC cultures was not related to increased medium acidity, because in the genetic background of the strains employed in these experiments (DBY746), the pH of stationary phase cultures established in 10% glucose was not significantly different from the pH of 2% glucose cultures (Table 1).

TABLE 1

| Strain | SC 10% glucose | SC 2% glucose | YPD 10% glucose | YPD 2% glucose |
|---|---|---|---|---|
| DBY746 | 3.32 (±0.2) | 3.38 (±0.03) | 4.72 (±0.11) | 4.79 (±0.09) |
| BY4742 | 3.19 (±0.02) | 3.79 (±0.59) | | |
| BY4741 | 3.18 (±0.06) | 4.17 (±0.07) | | |
| W303 | 3.17 (±0.01) | 3.57 (±0.01) | | |

Unexpectedly, the fraction of stationary phase cells with visible buds in 10% glucose SC cultures was reduced rather than increased compared to 2% glucose SC cultures (FIG. 3E). This likely reflects the accelerated death of dividing cells in SC medium containing 10% glucose Similar to the effects of elevated glucose in SC medium, wild type cells cultured in 10% glucose YPD medium exhibited a shorter CLS and increased O2-levels compared to cells cultured in 2% glucose YPD (FIG. 3F-G). However, in contrast to the reduced fraction of cells with visible buds detected in 10% glucose SC (FIG. 3E), a substantial increase in the fraction of visibly budded cells was detected in YPD cultures established in 10% glucose (FIG. 3H). As was the case for 10% glucose SC medium, the effects of 10% glucose in YPD medium were unrelated to changes in medium acidity, because the pH of these cultures did not differ significantly from the pH of YPD cultures established in 2% glucose (Table 1). Similar to the effects of inactivating Sch9p in cells cultured in 2% glucose SC (FIG. 1B-D), Sch9p inactivation extended CLS, reduced O2- and lowered the fraction of budded cells detected in wild type cells cultured in 10% glucose YPD (FIG. 3F-H). Since the CLS-shortening effects of 10% compared to 2% glucose are not related to acetic acid, we conclude that inactivation of Sch9p reduces O2- levels, enhances stationary phase G0/G1 arrest and extends CLS in 10% glucose medium by inhibiting glucose-dependent growth signaling, and not by causing resistance to acetic acid.

Wild type cells cultured in 2% glucose YPD medium also exhibited reduced levels of O2- compared to 2% glucose SC cultures (FIG. 10; also compare "WT 2% glu" in FIG. 3C with "WT 2% glu" in FIG. 3G). This likely reflects a reduced amount of acetic acid in stationary phase YPD cultures compared to SC cultures, because the pH of stationary phase YPD medium is substantially higher than the pH of SC medium (Table (Table1).1). Furthermore, unlike in 2% glucose SC cultures (FIG. 1B-C), in 2% glucose YPD cultures sch9Δ cells did not exhibit a longer CLS or reduced levels of O2- compared to wild type cells (FIG. 3F-G). This suggests that in 2% glucose SC cultures, inactivation of SCH9 extends CLS by inhibiting acetic acid induction of O2-.

We demonstrate that high glucose causes more frequent apoptotic elimination of dividing compared to non-dividing cells. In particular, the findings described above indicate that both glucose and acetic acid shorten CLS in concert with elevated levels of O2- and less efficient growth arrest of stationary phase cells in G0/G1. However, the reduced fraction of budded cells detected in 10% glucose compared to 2% glucose SC cultures (FIG. 3E) is not consistent with a general relationship between enhanced growth signaling, increased O2- and less efficient G0/G1 arrest. Budding yeast cells die in stationary phase by an apoptosis-like mechanism [36,37]. The substantial increase in the fraction of stationary phase wild type cells with visible buds in 10% glucose YPD (FIG.

3H) raised the possibility that the reduced fraction of budded cells in 10% glucose SC might be related to the very short CLS observed in these cultures and frequent apoptotic elimination of budded cells. Consistent with this possibility, PI staining of cells in 10% glucose SC stationary phase cultures revealed a 6-fold increase in the fraction of visibly budded cells that were dying compared to cells that did not have visible buds (FIG. 4A). This is substantially larger than the ~2-fold increase in budded compared to unbudded cells that stain with PI in 2% glucose SC cultures (FIG. 7). Furthermore, at day 2 of medium depletion, cells in 10% glucose SC cultures were more frequently undergoing apoptosis compared to cells in 2% glucose SC indicated by increased apoptotic degradation of DNA. In fact almost all the cells in 10% glucose cultures harbored substantially less than the complete G1 complement of DNA required for continued viability (FIG. 4B). Electron microscopic visualization of stationary phase cells cultured in 2% glucose YPD medium revealed that some cells exhibited fragmented nuclei indicative of apoptosis as well as an irregular cell shape indicating deterioration of the cell wall structure (FIGS. 4C and D). This contrasted with the appearance of intact nuclei and cell walls in non-apoptosing cells (FIG. 4E). In some cases, disruption of the cell wall structure was detected at specific sites in apoptosing cells (FIG. 4D; arrow) that may correspond to the location of a bud that broke off in cells undergoing apoptosis. A decline in numbers of cells in 10% glucose SC stationary phase cultures from day 1 to day 3 measured by counting particles (FIG. 4F) confirmed that similar to mammalian cells, budding yeast cells undergoing apoptosis eventually are completely destroyed. We conclude that high glucose reduces the efficiency of G0/G1 arrest in stationary phase and preferentially kills dividing cells, and that the reduced number of cells with visible buds in 10% glucose SC cultures is caused by the specific and rapid apoptotic destruction of cells that failed to arrest growth in G0/G1.

We demonstrate that superoxide anions inhibit stationary phase G0/G1 arrest. In connection with this, the inverse relationship between levels of O2- and the frequency with which cells arrest in G0/G1 when they enter stationary phase under a variety of experimental conditions (summarized in Table 2) suggests that O2- inhibits G0/G1 arrest. To test this hypothesis, we examined the effects of experimental manipulations that directly alter levels of O2- independently of changes in growth signaling pathways. sod2Δ cells exhibited a significantly shorter CLS (Figure (FIG. 5A) accompanied by increased O2- (FIG. 5B) and less efficient G0/G1 arrest (FIG. 5C) in stationary phase. Sod2p expression is elevated in sch9Δ cells, and deletion of SOD2 from sch9Δ cells partially suppresses their longevity phenotype ([4]; FIG. 5D). sch9Δ sod2Δ double mutant cells also exhibited an intermediate level of O2- compared to wild type or sch9Δ cells (FIG. 5E) accompanied by a stationary phase G0/G1 arrest that was intermediate between that of wild type and sch9Δ cells (FIG. 5F). Thus, a quantitative relationship exists between levels of O2- and frequency of G0/G1 arrest in sod2D, sch9D sod2Δ and wild type cells.

We also asked whether treatment of cells with the antioxidant N-acetylcysteine (NAC) would extend CLS and increase the efficiency of stationary phase G0/G1 arrest in association with reduced levels of superoxide. Surprisingly, NAC shortened CLS in a dose-dependent fashion in wild type, but not sch9Δ cells (FIG. 5G). The shorter CLS conferred by NAC in wild type cells occurred in concert with dose-dependent increases rather than decreases in levels of O2- (FIG. 5H). Similar pro-oxidant effects of the antioxidants α-tocopherol and coenzyme Q10 were recently reported in budding yeast, and induction of O2- by NAC has been reported in mammalian cells as well. Increased O2- in wild type cells exposed to NAC was accompanied by a parallel dose-dependent increase in the fraction of cells with visible buds (FIG. 5I). NAC-induced increases in O2- and frequency of G0/G1 arrest in stationary phase were absent in sch9Δ cells (FIGS. 5H and I; "sch9Δ"). The absence of NAC effects in sch9Δ cells expressing elevated levels of Sod2p [4] suggests that in wild type cells, the effects of NAC are related to increased amounts of O2- and not to unrelated toxic effects of this compound. In contrast, cells in which the catalases Cta1p or Ctt1p had been inactivated, which exhibit reduced levels of O2- in stationary phase and a longer CLS [8], also exhibited fewer visible buds (FIG. 5J). Similarly, cells treated with the antioxidant glutathione (GSH) also exhibited fewer visible buds (FIG. 5K) in concert with reduced levels of O2- (FIG. 5L). We conclude that O2- inhibits growth arrest of stationary phase cells in G0/G1.

Figure 6:
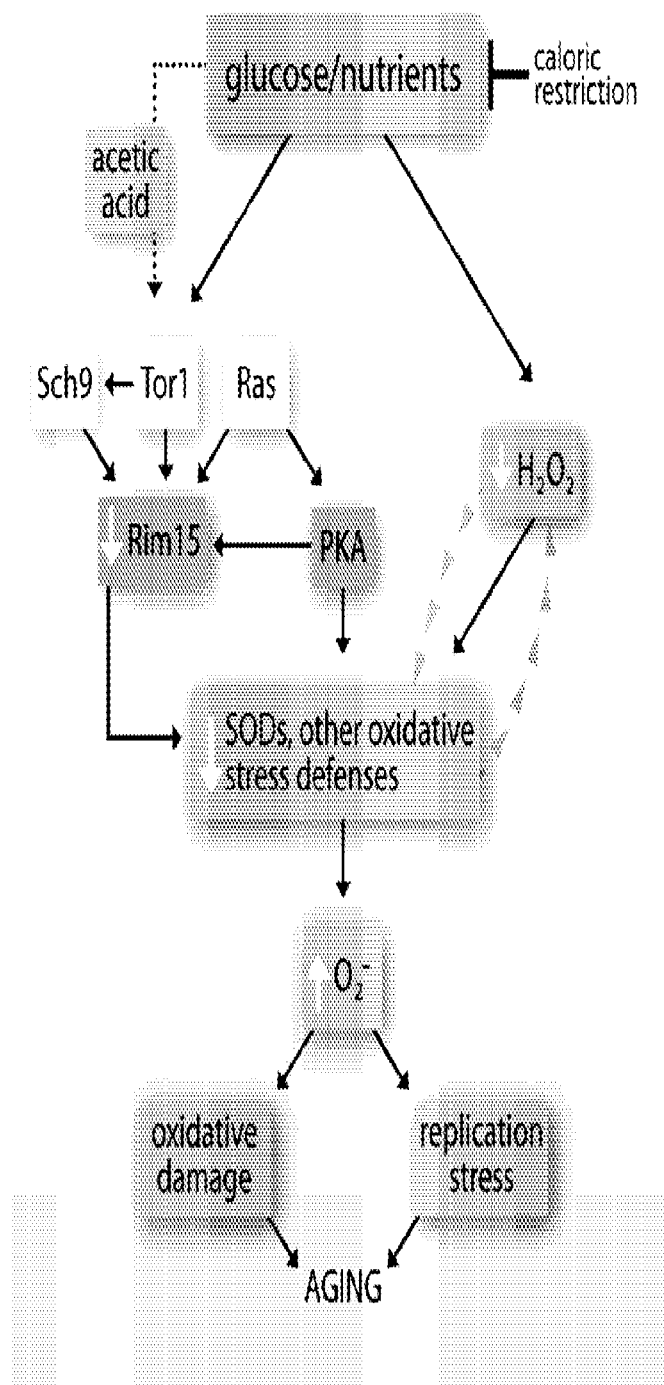
FIG. 6: Impact of growth signaling pathways and caloric restriction on chronological lifespan in budding yeast. Glucose and other nutrients signal growth through conserved Sch9p-, Tor1p- and Ras-dependent pathways that inhibit Rim15p and its induction of oxidative stresses defenses, leading to elevated O2- that cause oxidative damage and DNA replication stress. Acetic acid induces O2- by activating the same pathways. Caloric restriction attenuates signaling through these pathways and also induces H2O2 that activates SODs and reduces levels of O2- independently of Rim15p. In caloric restriction conditions, H2O2 that accumulates as a byproduct of increased SOD activity might stimulate SOD activity further by a self-amplifying mechanism.

We analyzed growth signaling and superoxide anions in a chronological aging model. Our findings reveal that under a variety of experimental conditions, an inverse relationship exists between budding yeast CLS and intracellular levels of O2- (summarized in Table Table2)2) that points to O2- accumulating downstream of growth signaling as a primary cause of chronological aging. A role for growth signaling-induced O2- in chronological aging is consistent with earlier reports that CR extends CLS in part by downregulating Tor1p-, Ras2p- and Sch9p-dependent growth signaling pathways that inhibit the Rim15p kinase and its induction of oxidative stress defenses (FIG. 6). Our findings also indicate that the Rim15p-independent extension of CLS by CR reported earlier [7] is related to the induction of H2O2 that reduces O2- (FIG. 1G) by activating SODs independently of Rim15p (FIG. 6).

Figure 3:
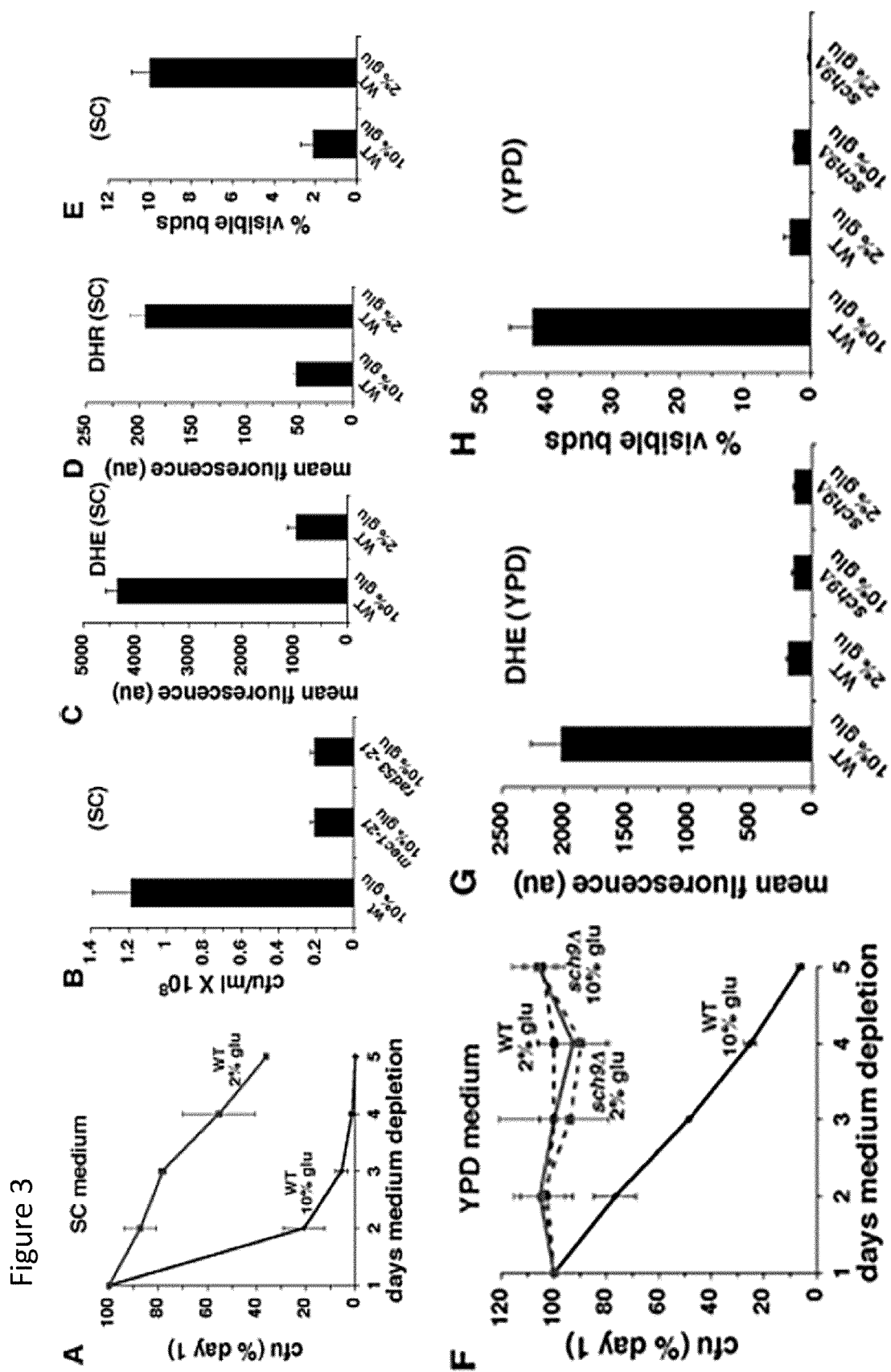
FIG. 3: Effects of high glucose (10%) in SC or YPD medium. (A) CLS of wild type cells in SC medium initially containing 2% or 10% glucose. (B) Reproductive capacity after 2 days of medium depletion of wild type, mec1-21 or rad53-21 cells cultured in SC medium containing 10% glucose. (C) Levels of O2- detected by DHE fluorescence in SC cultures of wild type cells at day 3. (D) Levels of H2O2 detected by DHR fluorescence in SC cultures at day 3. (E) Fraction of cells with visible buds in SC cultures at day 3 of medium depletion. (F) CLS of wild type and sch9Δ cells in YPD medium initially containing 2% or 10% glucose. (G) Levels of O2-detected by DHE fluorescence in YPD cultures at day 3. (H) Fraction of cells with visible buds in YPD cultures at day 3.
Figure 5:
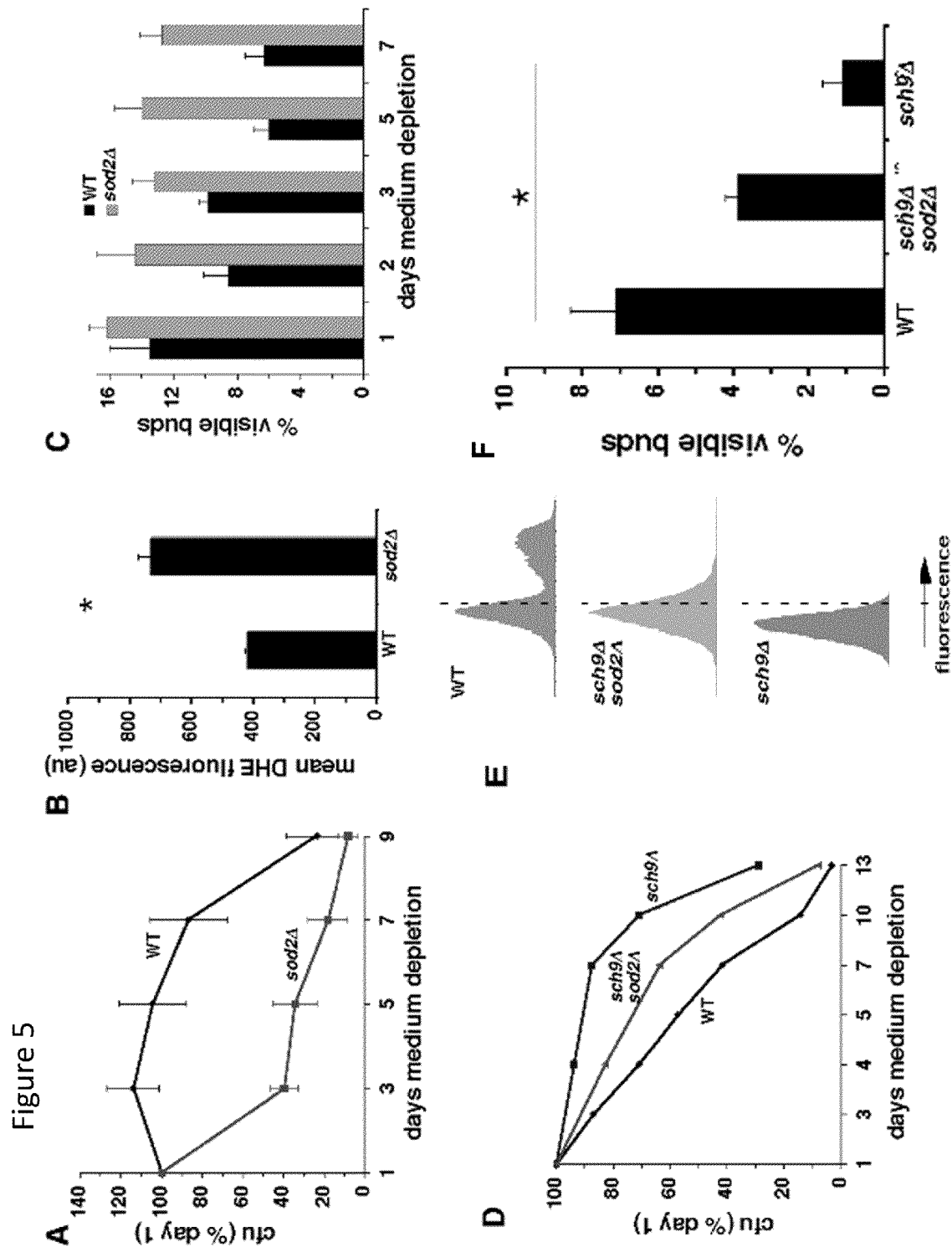
FIG. 5: O2- inhibit growth arrest of stationary phase cells in G0/G1 in parallel with a shorter CLS. (A) CLS of wild type and sod2Δ cells in 2% glucose SC medium. (B) Levels of O2- in wild type and sod2Δ cells detected by DHE fluorescence at day 3 of medium depletion. C. Fraction of cells with visible buds in wild type and sod2Δ cells at indicated times of medium depletion. (D) CLS of wild type, sch9Δ and sch9Δ sod2Δ cells. (E) Levels of O2- detected by DHE fluorescence in wild type, sch9Δ and sch9Δ sod2Δ cells at day 3 of medium depletion. (F) Fraction of cells with visible buds in wild type, sch9Δ and sch9Δ sod2Δ cells at day 3 of medium depletion. (G) Dose-dependent effects of NAC on CLS in wild type and sch9Δ cells. (H and I) Dose-dependent effects of NAC on O2- detected by DHE (H) and fraction of cells with visible buds (I) in wild type and sch9Δ cells at day 3 of medium depletion. (J) Fraction of cells with visible buds in wild type cells and the catalase mutants cta1Δ and ctt1Δ at day 3 of medium depletion. (K) Fraction of cells with visible buds at day 3 of medium depletion that were treated or not treated with the anti-oxidant GSH beginning at day 0. (L) Effect of GSH in wild type cells on levels of O2- indicated by DHE fluorescence at day 3 of medium depletion.

Our data are consistent with a role for acetic acid toxicity as a determinant of CLS in 2% glucose medium. However, acetic acid causes O2- to accumulate in stationary phase cells, because buffering SC medium to a higher pH, which extends CLS, reduces levels of O2-. O2-levels are similarly reduced in cells in YPD (FIG. 9), which in addition to maintaining a higher medium pH (Table 1) exhibit a longer CLS (FIG. 3). O2- accumulating in stationary phase cells is toxic, because experimental manipulations that directly elevate O2- levels (inactivation of Sod2p or exposure to NAC) shorten CLS (FIG. 5).

Acetic acid and/or intracellular acidification induce the same TOR- and RAS-dependent growth signaling pathways induced by glucose, and the induction of O2- by acetic acid is likely a consequence of acetic acid-induced growth signaling. A role for RAS-dependent growth signaling in acetic acid toxicity is consistent with an earlier report that the enhanced stationary phase viability of ras1Δ and/or ras2Δ cells cultured in SC medium is absent in YPD cultures or in cultures buffered to a higher pH. Our finding that CLS extension in sch9Δ compared to wild type cells cultured in 2% glucose SC (FIG. 1B) is similarly absent when these cells are cultured in 2% glucose YPD, (FIG. 3F), which also maintains a higher pH, indicates that acetic acid also triggers Sch9p-dependent growth signaling pathways. Therefore, the protective effects against acetic acid toxicity in unbuffered 2% glucose medium associated with inactivating Ras1p, Ras2p and Sch9p are likely due to downregulation of growth signaling by acetic acid and consequent upregulation of SODs and other oxidative stress defenses by Rim15p (FIG. 6). It has been proposed that the effects of acetic acid on CLS are specific for this form of acid. However, deletion of RAS1 and RAS2 also protects against acid stress induced by hydrochloric acid. Furthermore, Ras2p-dependent growth signaling is triggered by the acidifying protonophore 2,4-dinitrophenol. Low pH also induces AKT activity in human cells, and as we noted earlier, growth signaling by low pH that depends on RAS, AKT and other oncogenes underlies a number of pathological states in humans, including cancer. Thus, acetic acid toxicity in budding yeast corresponds to a conserved mitogen-like response to low pH, and not just acetic acid, that mimics the sustained activation of oncogenes in complex eukaryotes.

Our data also reveal superoxide anions and the effects of enhanced growth signaling by high glucose. In particular, in mammalian cell cultures, high levels of glucose that mimic the effects of hyperglycemia induce DNA damage, AKT-dependent growth signaling, increased O2- and senescence. Each of these effects has been implicated in aging and age-related diseases linked to hyperglycemia and/or excess calorie intake, including cancer, diabetes and cardiovascular disease. High glucose also promotes aging in *C. elegans* in association with increased O2-. The induction of elevated O2- and a shorter CLS by glucose signaling has been implicated in aging in the fission yeast *S. pombe* as well. The increased levels of O2- (FIGS. 3C and G) and shorter CLS (FIGS. 3A and F) induced by 10% glucose in either SC or YPD medium establish budding yeast as an additional model for investigating the effects of elevated glucose on aging and age-related diseases. These effects are mediated in part by Sch9p-dependent signaling by glucose because in 10% glucose YPD cultures, sch9Δ cells exhibit a longer CLS and less O2- compared to wild type cells (FIG. 3) in the absence of changes in pH compared to 2% glucose YPD cultures.

Changes in levels of acetic acid also do not play a role in the CLS-extending effects of increased H2O2 induced by CR. The longer CLS in 2% compared to 10% glucose SC or YPD cultures in the absence of a change in medium pH reveals an additional mechanism by which CR extends CLS in budding yeast related to reduced growth signaling by glucose rather than acetic acid. CR is most often defined in yeast experiments as a decrease in the glucose content of medium below 2%. However, in their natural environment yeasts are likely exposed to higher concentrations of glucose and other sugars that trigger growth signaling. For example, the glucose and fructose content of grapes can exceed 13% and the sugar content of overripe plantains approaches 27%. Thus, culturing cells in 2% compared to 10% glucose medium can be considered a physiologically relevant form of CR that depends on reduced growth signaling by glucose rather than acetic acid. This form of CR is broadly relevant to CR in complex eukaryotes.

Our data reveal relationships between growth signaling, superoxide anions and DNA replication stress. Specifically, the longstanding free radical theory of aging predicts that the pro-aging effects of O2- are caused by oxidative damage to macromolecules. However, the reduced levels of O2- and extended CLS produced by inactivation of catalases are accompanied by increased, rather than decreased oxidative damage. Conversely, the shorter CLS detected in sod2Δ and other cells harboring defective oxidative stress defenses is not accompanied by general increases in oxidative damage to macromolecules. A similar disconnect between oxidative damage and longevity is observed in naked mole rats, which exhibit a ~10-fold longer lifespan compared to mice despite the presence of high levels of oxidative damage. This suggests that the pro-aging effects of oxidative stress are not always a direct consequence of oxidative damage.

The inverse relationship between CLS and levels of O2- we detected under a variety of experimental conditions is accompanied by a similar inverse relationship between levels of O2- and frequency of G0/G1 arrest in stationary phase (Table 2). This points to an alternative, but not mutually exclusive possibility—that the age-promoting effects of O2- are related in part to inhibition by O2- of growth arrest of stationary phase cells in G0/G1, leading to more frequent growth arrest in S phase instead, where cells suffer replication stress.

TABLE 2

| Experiment | Superoxide anions | G0/G1 arrest |
|---|---|---|
| Longer CLS: | | |
| Deletion of SCH9 | ↓ | ↑ |
| Deletion of TOR1 | ↓ | ↑ |
| Deletion of RAS2 | n.d. | ↑ |
| Caloric restriction | ↓ | ↑ |
| Buffering pH to 6.0 | ↓ | ↑ |
| GSH | ↓ | ↑ |
| Deletion of CTA1 | ↓ | ↑ |
| Deletion of CTT1 | ↓ | ↑ |
| Shorter CLS: | | |
| Deletion of PDE2 | ↑ | ↓ |
| Deletion of SNF1 | ↑ | ↓ |
| Deletion of RIM15 | ↑ | ↓ |
| Deletion of SIC1 | ↑ | ↓ |
| Deletion of SOD2 | ↑ | ↓ |
| High glucose | ↑ | ↓ |
| N-acetylcysteine | ↑ | ↓ |

The inhibitory effects on G0/G1 arrest in stationary phase of experimental manipulations that more directly impact levels of O2- compared to alterations in growth signaling pathways (FIG. 5) are consistent with this model.

Based on measurements of the fraction of stationary phase cells with visible buds, Madia et al. proposed that the effects on chronological aging related to replication stress are minor compared to other pro-aging factors [Madia F, et al. J. Cell Biol. 2009; 186:509-523]. In fact, the magnitude of inhibitory effects on G0/G1 arrest in stationary phase related to O2- is larger than suggested by counting cells with visible buds in stationary phase, for several reasons. First, cells die in stationary phase cultures via an apoptosis-like mechanism ([FIG. 4B-D) that eventually destroys cells (FIG. 4F). The preferential death of cells that failed to arrest in G0/G1 (FIGS. 7 and 4A) leads to underestimates of the fraction of these cells. Second, our data suggest that as the budding yeast cell wall deteriorates during apoptosis, buds break off of mother cells (FIG. 4D), which would lead to additional underestimates of the fraction of cells with visible buds. Third, cells in early S phase with small buds are difficult to distinguish microscopically from unbudded cells that have truly arrested in G0/G1. Consequently, at least some of the dying cells that do not have visible buds in stationary phase in our experiments have not arrested in G0/G1.

According to a recent study, treatment of cells with low levels of hydroxyurea, which inhibits a protein essential for DNA replication (ribonucleotide reductase) shortens CLS by 20-27% [Palermo V, Cell Cycle. 2010; 9:3991-6]. Furthermore, increased apoptosis of stationary phase cells harboring a mutation in the replication stress protein Mec1 is suppressed by ectopic expression of the RNR1 gene encoding ribonucleotide reductase. Therefore, in principle, replication stress caused by reduced dNTP pools can substantially shorten CLS. Replication stress as a determinant of CLS is consistent with the observation that stationary phase cells that fail to arrest in G0/G1 die faster than unbudded cells (FIG. 7). The rate at which dividing cells die in stationary phase is accelerated further when growth signaling and levels of O2- are enhanced by high glucose (FIG. 4A), which also triggers DNA damage responses (FIG. 3B). These findings indicate that the toxic effects of O2- in stationary phase cells are caused in part by DNA damage specifically in cells that failed to growth arrest in G0/G1.

A role for replication stress in chronological aging is also consistent with an earlier report by Allen et al. that non-quiescent stationary phase cells separated from denser quiescent cells by density gradients more frequently undergo apoptosis and exhibit elevated expression of genes encoding proteins that respond to replication stress [Allen C, et al. J. Cell Biol. 2006; 174:89-100]. It is not consistent with the results of a recent genetic screen that identified budding yeast deletion mutants that exhibit an extended CLS in the absence of more frequent stationary phase growth arrest in G0/G1 [Fabrizio P., et al. PLoS Genet. 6:e1001024]. However, this screen also failed to identify the numerous deletion strains with inactivated growth signaling pathways, including sch9Δ, that were previously reported to have an extended CLS. In fact, in this recently published study, ras2Δ cells that earlier studies indicated are long-lived in the CLS model exhibited a substantially shorter CLS compared to wild type cells.

Replication stress as a determinant of CLS also is not consistent with the recent claim by Madia et al. that the denser fraction of stationary phase cells, which according to Allen et al. are quiescent and exhibit fewer signs of genome instability-promoting replication stress, paradoxically exhibit an elevated mutation frequency compared to "non-quiescent" cells. We note that the experiments of Allen et al. employed YPD medium, which prolongs CLS compared to CLS in SC medium (FIG. 3) and maintains a fraction of quiescent cells exhibiting a higher density for weeks. In contrast, Madia et al. employed SC medium in their experiments. Close inspection of the data in FIG. 22 of Madia et al. indicates that although a denser fraction of cells initially accumulated at day 1 of stationary phase in their experiments, unlike the experiments of Allen et al., this fraction declined and the fraction of less dense non-quiescent cells increased during the next several days of stationary phase. Furthermore, the number of stationary phase cells in S phase increased during this same period of time (Madia et al.). Although the fraction of budded cells in both "quiescent" and "non-quiescent fractions continues to decline with increasing time in stationary phase despite an overall increase in cells in S phase, this likely reflects the specific apoptotic destruction of budded cells. In fact, flow cytometry measurements by Madia et al. of the DNA content of "quiescent" and "non-quiescent" wild type cells clearly indicate that at the three and five day stationary phase time points they employed to measure mutation frequency in their experiments, most of the wild type cells they defined as "quiescent" that exhibited a higher mutation frequency also harbored significantly more DNA compared to "non-quiescent" wild type cells, and thus were more frequently in S phase (FIG. S1B of Madia et al.; compare "Lower Fraction" (quiescent) histograms with "Upper Fraction" (non-quiescent) histograms at each time point). Thus, in contrast to the experiments of Allen et al., the initially denser cells Madia et al. refer to as "quiescent" do not remain quiescent for more than a few days, most likely due to increased growth signaling by the larger amounts of acetic acid accumulating in SC medium compared to the YPD medium employed in the experiments of Allen et al. In the absence of nutrients required for efficient DNA replication in stationary phase cultures, entry of these cells into S phase is a recipe for replication stress and mutations.

We also contemplate growth signaling, oxidative stress and replication stress and aging in complex organisms. In particular, the induction of insulin/IGF-1-like growth signaling pathways that depend on RAS, AKT, mTOR and other oncogenic proteins has been implicated in aging and a number of age-related diseases in humans, including many for which hyperglycemia and/or excess calorie intact are risk factors. In addition to elevated levels of ROS, DNA replication stress has been implicated in some of these diseases as well. For example, sustained oncogenic signaling that leads to growth arrest in S phase has been implicated in the senescent state of preneoplastic cells. Similarly, inappropriate activation of growth signaling pathways in tauopathies and other neurodegenerative disorders promotes unscheduled entry of postmitotic neurons into S phase, where these cells also likely undergo replication stress. Thus, as in budding yeast, growth signaling may impact aging in more complex organisms, including humans, by inducing replication stress, in addition to oxidative stress.

As in budding yeast, replication stress in mammalian cells may be related to O2-inhibition of quiescence. Consistent with this possibility, MnSOD-defective mouse cells driven into a non-dividing state by contact inhibition exhibit elevated levels of O2-, a higher fraction of S phase cells and increased apoptosis [Sarsour E H, et al. Aging Cell. 2008; 7:405-417]. Furthermore, O2-induced by hyperglycemia [Zanetti M, et al. Arterioscler Thromb Vasc Biol. 2001; 21:195-200] or by a metabolite of polychlorinated biphenyls that cause cancer [Chaudhuri L, et al. Environ Int. 2010; 36:924-930] inhibit DNA replication. These findings have important implications for understanding aging and age-related diseases. For example, although DNA replication stress now is generally accepted as a factor that contributes to tumorigenesis downstream of oncogene activation, it is not considered to be an initiating event. However, high glucose inhibits progression of endothelial cells through S phase, and as in our yeast experiments presented here, also induces DNA damage in human mesothelial cells. It is feasible, therefore, that hyperglycemia and other factors can initiate tumorigenesis by inducing replication stress that leads to mutational activation of oncogenes. Thus, the compositions and methods of the present invention are expected to be able to inhibit such replication stress and provide a therapeutic and/or prophylactic effect against these and other stress-related diseases. They are also expected to inhibit inflammatory responses mediated by superoxide anions. For example, in addition to reducing superoxide anions in *S. cerevisiae*, PUBMED compounds MLS000326642 and MLS000700045 and the sirtuin inhibitor SRT1720 inhibit interleukin-6 release from human macrophages.

EXAMPLE 2

This Example relates to the assay used to screen PubChem compounds to identify those compounds that can act as caloric restriction mimetics, and as such would be useful for at least the reasons described in the Examples above. The screen was designed to identify compounds that mimic caloric restriction by down-regulating growth signaling pathways, thus reducing the accumulation of superoxide anions and promoting a tighter growth arrest in G1. The primary readout for this screen was measurements of superoxide changes using the fluorogenic compound dihydroethidium (DHE). The assay is in one embodiment a high throughput assay (flow cytometry) wherein small molecules are screened to determined their ability to reduce basal levels of intracellular O2- in stationary phase budding yeast cells, preferably by at least three standard deviation from negative controls. In the invention, live yeast cells as otherwise provided herein are grown in media in the presence of other nutrients and components as otherwise described herein at a liquid-air interface in wells of a high throughput flow cytometry microtiter plate and compounds are screened by high throughput flow cytometry to determine which compounds inhibit the production of superoxide from the yeast grown in media. In one embodiment, the microtitre plate is at least a 384-well microtiter plate. A preferred embodiment of the assay is a phenotypic assay for detection of ROS inhibitors in a yeast model of senescence that is performed according to the following parameters: Solutions required per 384-well microtiter plate (for analysis of 320 compounds) include: 6.3 mL SC medium, 1.8 mL yeast (OD=0.4) in SC medium, 0.2 mL 3-AT control (15 milliM in media), 12 mL 5 microM DHE in PBS with 0.1% BSA. In a divided reservoir plate (Phenix catalog #RR13027; columns 1,2,23, and 24 have individual reservoirs while 3-22 are have a shared reservoir) SC medium is added to the large center reservoir (22 mL for 1 plate or 29 mL for 2 plates, etc.) and to column 2, and the 3-AT to the column 1 reservoir (1.2 mL). Columns 23 and 24 are left empty for use as wash stations. Using a 384-tip head on the Biomek FXp liquid handler (Beckman Coulter, USA), 17 microL is transferred to a 90 microL deep well 384-well plate (Greiner catalog #784201). Using a 200 nanoL pin tool (V &P Scientific) on the Biomek FXp, the library compounds are transferred from the compound plate to the assay plate (final assay concentration is 10 milliM). Using a Nanoquot (BioTek, USA) liquid handler, 5 microL of yeast solution is added to columns 1-22 of the assay plate. Assay plates are sealed with a breathable plastic membrane and incubated in a humidified (95%) incubator at 30 degrees C. for 7 days. On the day the plate is read, a dilution plate is prepared by transferring 30 microL milliM DHE in PBS with 0.1% BSA to every well in a 384-well 90 microL volume plate. Using the 384 tip head on the Biomek FXp, the assay plate contents are mixed to re-suspend yeast, then a volume of 3 microL is transferred to the dilution plate. Plates are analyzed by flow cytometry after 5-60 minutes using the HyperCyt [Edwards et al 2001] (IntelliCyt, USA) autosampler and the Cyan (Beckman Coulter, USA) flow cytometer using the 488 nanometer laser and the FL3 (PE-Texas Red, 613 nanometer) filter set. We used a 7 day incubation in 384 well plates in media containing 7% glucose upside down in a 95% humidified incubator with two breatheEZ membranes to seal the plate. The inclusion of 7% glucose to the media described above and 7 day conditions as well as growing the yeast at a liquid-air interface are believed to be important to obtain a high signal for superoxide in untreated cells. Incubating the plates upside down is believed to be necessary due to the lack of mixing so that the yeast cells would grow at the air-liquid interface where the most oxygen exchange could occur. Plates incubated right side up produced very little superoxide, most likely due to poor oxygenation of media in plates that are not mixed/agitated. The humidified incubator was believed to be necessary because the total volume in each well is 20 microliters and rate of evaporation studies proved that the wells were dried up by the end of day 3. By increasing the humidity to 95% using a household humidifier on a habitat monitoring device the evaporation over 7 days was reduced to a loss of less than 20%. To compensate for this the assay volume at the beginning of the 7 days was set at 25 microliters. It was additionally shown that two breathe-EZ membranes slowed the evaporation further. During development 3-aminotriazol, was used as an alternative control for isonicotinamide, at 10 mM concentrations, but it was determined that a 20 mM concentration provided a more robust and reproducible decrease in superoxide signals. Lastly it was found that a concentration of 25 microM DHE was too high and produced a high background signal and so it was found that 5 microM was the ideal concentration. Using this screen, approximately 330 k compounds were screened 587 compounds were identified as potential hits. 986 compounds were selected for further analysis (the 587 "hits" and 399 structurally similar compounds, 865 were available and used in confirmatory testing. Of the 865 compounds retested 26 reconfirmed and those, in addition to 20 structurally related compounds, were assayed in dose response assays from 0.004 uM to 30 uM. 29 compounds able to cause a significant decrease in superoxides were identified and an additional 47 compounds were identified for additional testing as probable hits based on structure similarities to the confirmed hits. The compounds identified by dose dependency are identified by their respective PubChem numbers as: MLS002320508, MLS000554700, MLS002554375, MLS002554453, MLS002554454, MLS002554450, MLS000700045, MLS001049309, MLS001044416, MLS001164912, MLS000584128, MLS000863638, MLS000584128, MLS000768911, MLS001208198, MLS001044341, MLS001044346, MLS001173415, MLS000418506, MLS000033501, MLS000100785, MLS000326584, MLS000326622, MLS000326642, MLS000663774, MLS000662516, MLS000779260, MLS000121367; MLS000737174, MLS002638803, MLS001044337, MLS000768124, MLS000756830, MLS001048992, MLS001164888, MLS002153505, MLS000595212, MLS001003683, MLS000855890, MLS001044354, and MLS001176565.

Also disclosed are dose response curves for these compounds, which are presented in FIGS. 11-20, along with calculated IC50s for each compound. These compounds can be formulated into pharmaceutical preparations using standard methods and reagents, excipients, and the like. Likewise, given the benefit of the present disclosure, dosing parameters can be determined by the skilled artisan, taking into account such factors as the size, sex and age of the individual, the chemical composition of the particular compound(s) used in the method, and other factors that can be determined using ordinary techniques.

While the foregoing description of the invention has been shown and described with reference to certain preferred embodiments thereof, it will be understood by those skilled in the art that various changes in form and details may be made therein without departing from the spirit and scope of the invention as described.

The invention claimed is:

1. A method for reducing intracellular superoxide anions in a eukaryotic organism comprising administering to the eukaryotic organism a composition comprising a compound having a structure, wherein $R^{10}$ is H or an alkyl.

* * * * *

UNITED STATES PATENT AND TRADEMARK OFFICE
CERTIFICATE OF CORRECTION

PATENT NO.        : 9,034,857 B2                         Page 1 of 1
APPLICATION NO.   : 13/636785
DATED             : May 19, 2015
INVENTOR(S)       : Burhans et al.

It is certified that error appears in the above-identified patent and that said Letters Patent is hereby corrected as shown below:

In the claims:

Column 24, lines 54-58, claim 1 should read:

--1. A method for reducing intracellular superoxide anions in a eukaryotic organism comprising administering to the eukaryotic organism a composition comprising a compound having a structure

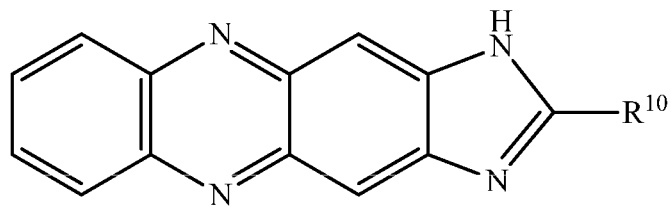

, wherein $R^{10}$ is H or alkyl.--

Signed and Sealed this
Eighth Day of March, 2016

Michelle K. Lee
*Director of the United States Patent and Trademark Office*